US007700555B2

(12) United States Patent
Gunton et al.

(10) Patent No.: US 7,700,555 B2
(45) Date of Patent: Apr. 20, 2010

(54) METHODS OF TREATING DIABETES

(75) Inventors: Jenny Gunton, Sydney (AU); C. Ronald Kahn, West Newton, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 176 days.

(21) Appl. No.: 11/653,594

(22) Filed: Jan. 16, 2007

(65) Prior Publication Data

US 2007/0253904 A1 Nov. 1, 2007

Related U.S. Application Data

(63) Continuation-in-part of application No. PCT/US2005/024866, filed on Jul. 13, 2005.

(60) Provisional application No. 60/588,071, filed on Jul. 15, 2004, provisional application No. 60/624,928, filed on Nov. 4, 2004.

(30) Foreign Application Priority Data

Nov. 4, 2004 (AU) .............................. 2006906499

(51) Int. Cl.
*A61K 38/00* (2006.01)
*A61K 39/395* (2006.01)
*C07K 14/00* (2006.01)

(52) U.S. Cl. ........................ 514/12; 514/2; 424/158.1; 530/350

(58) Field of Classification Search ....................... None
See application file for complete search history.

(56) References Cited

U.S. PATENT DOCUMENTS

2005/0136465 A1* 6/2005 Clerc et al. .................... 435/6

FOREIGN PATENT DOCUMENTS

WO    WO 2006/019824    2/2006

OTHER PUBLICATIONS

Stewart et al. 1999. Diabetic Medicine. 16:93-112.*
Hotamisligil. Nature. 444:860-867.*
Medline Plus, www.nlm.nig.gov/medlineplus/print/ency/article/002072.htm, downloaded Dec. 30, 2008.*
Mickle et al. 2000, Med Clin North Am 84:597-607.*
Yan et al. 2000, Science 290:523-527.*
Hotamisligil. 2006.Nature. 444:860-867.*
Abbott and Buckalew, "Placental defects in ARNT-knockout conceptus correlate with localized decreases in VEGF-R2, Ang-1, and Tie-2," Dev. Dyn. 219(4):526-538 (2000).
Antonsson et al., "Constitutive function of the basic helix-loop-helix/PAS factor Arnt. Regulation of target promoters via the E box motif," J. Biol. Chem. 270(23):13968-13972 (1995).
Bruning et al., "Development of a novel polygenic model of NIDDM in mice heterozygous for IR and IRS-1 null alleles," Cell, 88(4):561-572 (1997).

Catrina et al., "Hyperglycemia regulates hypoxia-inducible factor-1alpha protein stability and function," Diabetes, 53(12):3226-3232 (2004).
Chapman-Smith et al., "Contribution of the Per/Arnt/Sim (PAS) domains to DNA binding by the basic helix-loop-helix PAS transcriptional regulators," J. Biol. Chem. 279(7):5353-62 (2004). Epub Nov. 24, 2003.
DeFronzo et al., "Pathogenesis of NIDDM. A balanced overview," Diabetes Care, 15(3):318-368 (1992).
Forsythe et al., "Activation of vascular endothelial growth factor gene transcription by hypoxia-inducible factor 1," Mol. Cell. Biol. 16(9):4604-4613 (1996).
Gunton et al., "Loss of ARNT/HIF1beta mediates altered gene expression and pancreatic-islet dysfunction in human type 2 diabetes," Cell, 122(3):337-349 (2005).
Hosoya et al., "Defective development of secretory neurones in the hypothalamus of Arnt2-knockout mice," Genes to Cells, 6(4):361-74 (2001).
Kozak et al., "ARNT-deficient mice and placental differentiation," Dev. Biol. 191(2):297-305 (1997).
Kulkarni et al., "Altered function of insulin receptor substrate-1-deficient mouse islets and cultured beta-cell lines," J. Clin. Invest. 104(12):R69-75 (1999).
Lauro et al., "Impaired glucose tolerance in mice with a targeted impairment of insulin action in muscle and adipose tissue," Nat. Genet. 20(3):294-298 (1998).
Maltepe et al., "Abnormal angiogenesis and responses to glucose and oxygen deprivation in mice lacking the protein ARNT," Nature, 386(6623):403-407 (1997).
Marfella et al., "Expression of angiogenic factors during acute coronary syndromes in human type 2 diabetes," Diabetes, 53(9):2383-2391 (2004).
Martin et al., "Role of glucose and insulin resistance in development of type 2 diabetes mellitus: results of a 25-year follow-up study," Lancet, 340(8825):925-929 (1992).

(Continued)

*Primary Examiner*—Manjunath N Rao
*Assistant Examiner*—Shulamith H Shafer
(74) *Attorney, Agent, or Firm*—Fish & Richardson P.C.

(57) ABSTRACT

The invention provides methods of screening for compounds that increase levels or activity of Aryl hydrocarbon Nuclear Receptor Translocator (ARNT) and/or Hypoxia Inducible Factor 1α (HIF1α), for the treatment and prevention of diabetes-related disorders, including type 1 and type 2 diabetes mellitus, impaired glucose tolerance, insulin resistance and beta cell dysfunction; compounds identified by said screening methods; and methods of using said compounds. Also included are methods for treating or preventing diabetes-related diseases using ARNT and/or HIF1α polypeptides and polynucleotides, and for using information regarding the expression, level or activity of ARNT and/or HIF1α in predictive medicine, e.g., diagnostic assays, prognostic assays, monitoring clinical trials, and pharmacogenetics.

15 Claims, 10 Drawing Sheets

OTHER PUBLICATIONS

Mauvais-Jarvis and Kahn, "Understanding the pathogenesis and treatment of insulin resistance and type 2 diabetes mellitus: what can we learn from transgenic and knockout mice?," Diabetes Metab. 26(6):433-48 (2000) Erratum in: Diabetes Metab. 27(2 Pt 1):176 (2001).

McCarthy and Froguel, "Genetic approaches to the molecular understanding of type 2 diabetes," Am. J. Physiol. Endocrinol. Metab. 283(2):E217-E225 (2002).

Moritz et al., "Apoptosis in hypoxic human pancreatic islets correlates with HIF-1alpha expression," Fed. Am. Soc. Exp. Bio. J., 16(7):745-7 (2002), Epub Mar. 26, 2002.

Nandi et al., "Mouse models of insulin resistance," Physiol. Rev. 84(2):623-647 (2004).

Okino et al., "Hypoxia-inducible mammalian gene expression analyzed in vivo at a TATA-driven promoter and at an initiator-driven promoter," J. Biol. Chem. 273(37):23837-23843 (1998).

Petersen et al., "Impaired mitochondrial activity in the insulin-resistant offspring of patients with type 2 diabetes," N. Engl. J. Med. 350(7):664-671 (2004).

Salceda et al., "Absolute requirement of aryl hydrocarbon receptor nuclear translocator protein for gene activation by hypoxia," Arch. Biochem. Biophys. 334(2):389-394 (1996).

Sreekumar et al., "Gene expression profile in skeletal muscle of type 2 diabetes and the effect of insulin treatment," Diabetes, 51(6):1913-1920 (2002).

Tomita et al., "Conditional disruption of the aryl hydrocarbon receptor nuclear translocator (Arnt) gene leads to loss of target gene induction by the aryl hydrocarbon receptor and hypoxia-inducible factor 1alpha," Mol. Endocrinol. 14(10):1674-81 (2000).

Yechoor et al., "Coordinated patterns of gene expression for substrate and energy metabolism in skeletal muscle of diabetic mice," Proc. Natl. Acad. Sci. U.S.A. 99(16):10587-92 (2002) Epub. Jul. 29, 2002.

Zelzer et al., "Insulin induces transcription of target genes through the hypoxia-inducible factor HIF-1alpha/ARNT," The EMBO Journal, 17(17):5085-5094 (1998).

Braun et al., "The regulation of the induction of vascular endothelial growth factor at the onset of diabetes in spontaneously diabetic rats," Life Sci., 69(21):2533-2542, (2001).

Imagawa et al., "Pancreatic biopsy as a procedure for detecting in situ autoimmune phenomena in type 1 diabetes: close correlation between serological markers and histological evidence of cellular autoimmunity," Diabetes, 50(6):1269-1273, (2001).

Levine and Perdew, "Aryl hydrocarbon receptor (AhR)/AhR nuclear translocator (ARNT) activity is unaltered by phosphorylation of a periodicity/ARNT/single-minded (PAS)-region serine residue," Mol. Pharmacol., 59(3):557-566, (2001).

* cited by examiner

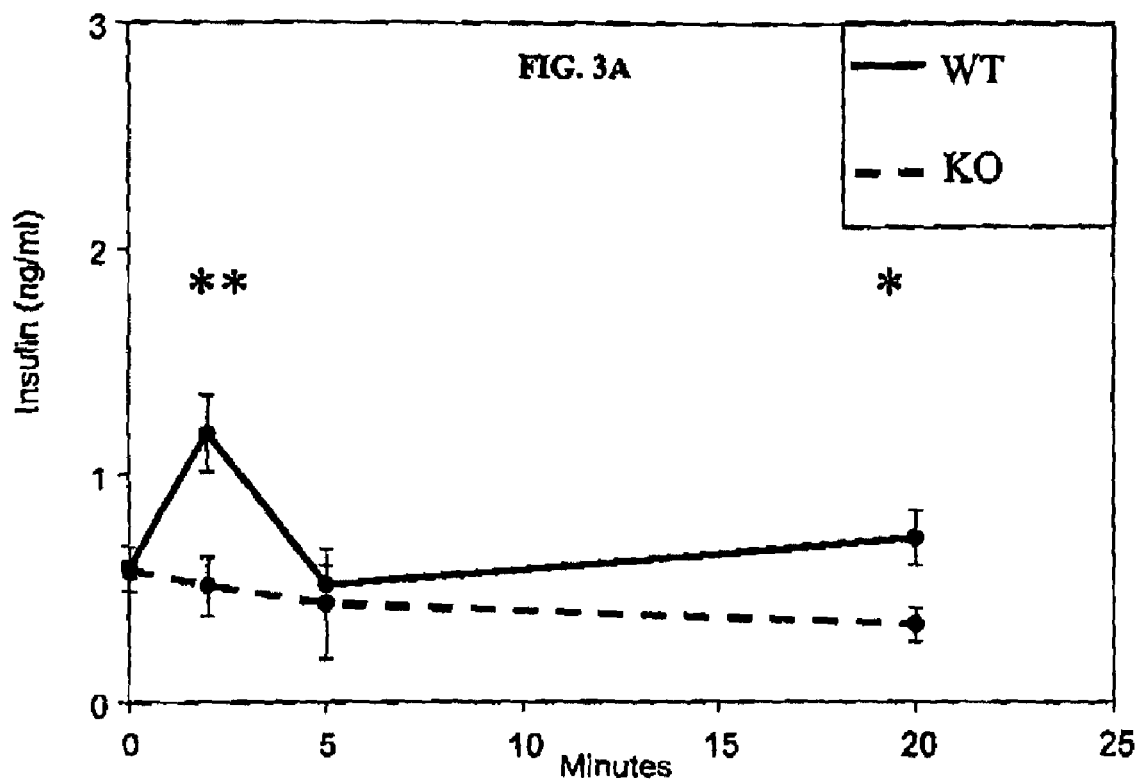
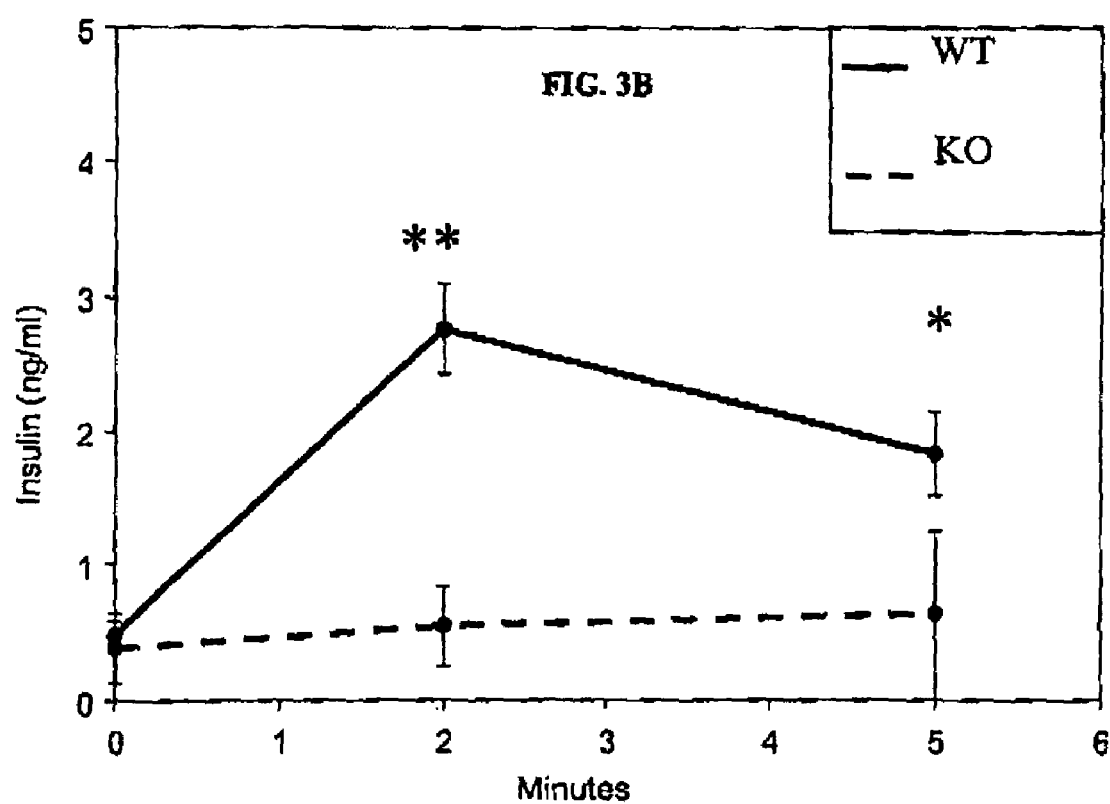

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 1
aaguggagga gcuguuguac a                                                 21

<210> SEQ ID NO 2
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 2
aagcgacgga acaagaugac a                                                 21

<210> SEQ ID NO 3
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 3
aaaggcugca gguaacuagu u                                                 21

<210> SEQ ID NO 4
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 4
aagaccaaca acuucuaaga g                                                 21
```

<210> SEQ ID NO 5
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 5
aagcacacag aacuggauau g                                           21

<210> SEQ ID NO 6
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 6
aaccuucagu gcuaugucuc u                                           21

<210> SEQ ID NO 7
<211> LENGTH: 4846
<212> TYPE: DNA
<213> ORGANISM: Homo sapiens

<400> SEQUENCE: 7
atcttggatt ccgcggtagc ggaggcggcg gtcaggcgcc gcttctgggg agtggccttt      60
cttttcccct ccctcccggt tcggtggcgg cggctcctcc cactgggggg gggggtggcg     120
cggcggcggt ggcatctgcg gccatggcgg cgactactgc caaccccgaa atgacatcag     180
atgtaccatc actgggtcca gccattgcct ctggaaactc tggacctgga attcaaggtg     240
gaggagccat tgtccagagg gctattaagc ggcgaccagg gctggatttt gatgatgatg     300
gagaagggaa cagtaaattt ttgaggtgtg atgatgatca gatgtctaac gataaggagc     360
ggtttgccag gtcggatgat gagcagagct ctgcggataa agagagactt gccagggaaa     420
atcacagtga aattgaacgg cggcgacgga acaagatgac agcctacatc acagaactgt     480
cagatatggt acccacctgt agtgccctgg ctcgaaaacc agacaagcta accatcttac     540
gcatggcagt ttctcacatg aagtccttgc ggggaactgg caacacatcc actgatggct     600
cctataagcc gtctttcctc actgatcagg aactgaaaca tttgatcttg gaggcagcag     660
atggcttttc tgtttattgt ccatgtgaga caggcagggt ggtgtatgtg tctgactccg     720
tgactcctgt tttgaaccag ccacagtctg aatggtttgg cagcacactc tatgatcagg     780
tgcacccaga tgatgtggat aaacttcgtg agcagctttc cacttcagaa atgcccctga     840
cagggcgtat cctggatcta aagactggaa cagtgaaaaa ggaaggtcag cagtcttcca     900
tgagaatgtg tatgggctca aggagatcgt ttatttgccg aatgaggtgt ggcagtagct     960
ctgtggaccc agtttctgtg aataggctga gctttgtgag gaacagatgc aggaatggac    1020
ttggctctgt aaaggatggg gaacctcact tcgtggtggt ccactgcaca ggctacatca    1080
aggcctggcc cccagcaggt gtttccctcc cagatgatga cccagaggct ggccagggaa    1140
gcaagtttg cctagtggcc attggcagat tgcaggtaac tagttctccc aactgtacag    1200
acatgagtaa tgtttgtcaa ccaacagagt tcatctcccg acacaacatt gagggtatct    1260
tcacttttgt ggatcaccgc tgtgtggcta ctgttggcta ccagccacag gaactcttag    1320
gaaagaatat tgtagaattc tgtcatcctg aagaccagca gcttctaaga gacagcttcc    1380

```
aacaggtagt gaaattaaaa ggccaagtgc tgtctgtcat gttccggttc cggtctaaga    1440
accaagaatg gctctggatg agaaccagct cctttacttt ccagaaccct tactcagatg    1500
aaattgagta catcatctgt accaacacca atgtgaagaa ctctagccaa gaaccacggc    1560
ctacactctc caacacaatc cagaggccac aactaggtcc cacagctaat ttacccctgg    1620
agatgggctc aggacagctg gcacccaggc agcagcaaca gcaaacagaa ttggacatgg    1680
taccaggaag agatggactg gccagctaca atcattccca ggtggttcag cctgtgacaa    1740
ccacaggacc agaacacagc aagccccttg agaagtcaga tggtttattt gcccaggata    1800
gagatccaag atttcagaa atctatcaca acatcaatgc ggatcagagt aaaggcatct    1860
cctccagcac tgtccctgcc acccaacagc tattctccca gggcaacaca ttccctccta    1920
ccccccggcc ggcagagaat tcaggaata gtggcctagc ccctcctgta accattgtcc    1980
agccatcagc ttctgcagga cagatgttgg cccagatttc ccgccactcc aaccccaccc    2040
aaggagcaac cccaacttgg acccctacta cccgctcagg cttttctgcc cagcaggtgg    2100
ctacccaggc tactgctaag actcgtactt cccagtttgg tgtgggcagc tttcagactc    2160
catcctcctt cagctccatg tccctccctg gtgcccaac tgcatcgcct ggtgctgctg    2220
cctaccctag tctcaccaat cgtggatcta actttgctcc tgagactgga cagactgcag    2280
gacaattcca gacacggaca gcagagggtg tgggtgtctg gccacagtgg cagggccagc    2340
agcctcatca tcgttcaagt tctagtgagc aacatgttca acaaccgcca gcacagcaac    2400
ctggccagcc tgaggtcttc caggagatgc tgtccatgct gggagatcag agcaacagct    2460
acaacaatga agaattccct gatctaacta tgtttccccc cttttcagaa tagaactatt    2520
ggggtgagga taaggggtgg gggagaaaaa atcactgttt gttttaaaa agcaaatctt    2580 tctgtaaaca gaataaaagt tcctctccct tcccttccct cacccctgac atgtaccccc    2640
tttcccttct ggctgttccc ctgctctgtt gcctctctaa ggtaacattt atagaagaaa    2700
tggaatgaat ctccaaggct tttaggactg tctgaaaatt tgaggctggg tgaagttaaa    2760 acaccttttcc ttatgtctcc tgacctgaaa ttgtatagtg ttgatttgtg ctgagatcaa    2820
gaggcaggtt agaagaacct gacatccact gtttgccttg gatagtatgg cttgtttttg    2880
gaaagaaatt ctgaagagag tggaggagag gagaaatgtc ctcatatttg aggaccatga    2940
aacattgtag gtatatatgg ggctttagca agtttgagca taggctcttt ttgctgcctg    3000
tgagcagtcc ctctggaaag aaacatgtga gtaagtgaga gagagtgtgt gtgtatgtgt    3060
gtgtgtgtgt gtgtgcgcac acatgcttct gtatttcact ctttctccct attagggagt    3120
tatgcaaaat ttgtccccga ttttaccttt gtctttctgt gtacttttca aagagtccta    3180
aggagttaaa tcttccaggt attttccact tagtattgca gccaagaat atttaaataa    3240 acgtctttgc tgcgcttgca tccatgccca gccaatatac aactgtaaag caaatataga    3300
aagtcggctg ttgatacgat tgtctgttat cgaacacatt cagtgataaa gctgggttac    3360
tgctgctttt ggtgctctca cctatctgg aagatctgca acattaccct aaataggctg    3420
gcaagataaa cactttctgg aacccgagac ttggccataa agataatgct gcattttct    3480 gtcagaatca catatgatgt gtgttctgta gaggttattt ctgcatggaa actcaacttc    3540
ttggattagc cgtcccagtg aaaatcctca ttgttggagt gtaaaccaaa tacgaagccc    3600
tcttgcaaag tagcctcttt catcccatac tcaaatacc cagtttagca agcaactgag    3660
atttaagtct ctctggccct aagaggtttt tcctctttgc tccctccaat cttgagattc    3720
ggttttgctt tagagtgcaa gtatcataat tccgtatgat agatgggcc tggacaccca    3780
```

-continued

```
tctcaacagg gtcacttggt aattaacaat agccatataa atgcggatac aggttactac    3840
cctcacccTT taccttcctc aggtaacagt cgtagatacc agcttttttt tttttttttt    3900
taaattggct ttggccagta gctaaagtgc aagactgaat taatgagaag atatattaaa    3960
tgtagtcata ggggactgag gagcaagggt ggccttgaag aggccaaagg aatgtccatt    4020
tgctgagttt cccttcctta tgtctccagt ctggtgccag gtagtggagt aaaaaaggag    4080
acagtttatt ttttttattct atgtgcacac ttacagtata catatatatt tatatcacaa    4140
tttacgaaac caaaaagttg agtttccaat ggaacccttg tttttttaata atcgactttt    4200 taaatgtgat caggactata atattgtaca gttattatag ggcttttggg gaaggggagg    4260
atagcgagaa gatgctctgg gggttttgtt tttgcttttc cttcagggtt ttattttTGA    4320
ctgttttgtt ttcttgttgg ccatttctgt attgctggca tctgtgctaa gctttacagt    4380
ggcaaaaata atgacatgta gcaaagattt tcaaacaaaa tattttttcc ttttgtaaaa    4440
tttcttgtgt tgtgtgatct tgattgcggc tttatcattc ctttccagtt cataaacaac    4500
aggcacccac aaccagagga atctatagtt taagctccag acatacaaac ataaggcaca    4560
ttgtgtcttt aatttcagga atcagaaatc atagggttct gatcacattg cacgcctccc    4620
ccctcacttg tcctcctgat cctgacacat tctgagtaac atcagcagga atgctctgac    4680
catgaggtgg gggttttggg gtgggcgttg cctgggttct tgggagagag gggaagagtc    4740
gggacttgaa aaccactagg gcacatctgg atgccttccc ccagtatgtc cttttctgga    4800
ttaaaatgag tgaaatttaa actgaaaaaa aaaaaaaaaa aaaaaa                   4846
```

<210> SEQ ID NO 8
<211> LENGTH: 789
<212> TYPE: PRT
<213> ORGANISM: Homo sapiens

<400> SEQUENCE: 8

```
Met Ala Ala Thr Thr Ala Asn Pro Glu Met Thr Ser Asp Val Pro Ser
 1               5                  10                  15

Leu Gly Pro Ala Ile Ala Ser Gly Asn Ser Pro Gly Ile Gln Gly
            20                  25                  30

Gly Gly Ala Ile Val Gln Arg Ala Ile Lys Arg Arg Pro Gly Leu Asp
        35                  40                  45

Phe Asp Asp Asp Gly Glu Gly Asn Ser Lys Phe Leu Arg Cys Asp Asp
    50                  55                  60

Asp Gln Met Ser Asn Asp Lys Glu Arg Phe Ala Arg Ser Asp Asp Glu
65                  70                  75                  80

Gln Ser Ser Ala Asp Lys Glu Arg Leu Ala Arg Glu Asn His Ser Glu
                85                  90                  95

Ile Glu Arg Arg Arg Arg Asn Lys Met Thr Ala Tyr Ile Thr Glu Leu
            100                 105                 110

Ser Asp Met Val Pro Thr Cys Ser Ala Leu Ala Arg Lys Pro Asp Lys
        115                 120                 125

Leu Thr Ile Leu Arg Met Ala Val Ser His Met Lys Ser Leu Arg Gly
    130                 135                 140

Thr Gly Asn Thr Ser Thr Asp Gly Ser Tyr Lys Pro Ser Phe Leu Thr
145                 150                 155                 160

Asp Gln Glu Leu Lys His Leu Ile Leu Glu Ala Ala Asp Gly Phe Leu
                165                 170                 175

Phe Ile Val Ser Cys Glu Thr Gly Arg Val Val Tyr Val Ser Asp Ser
```

-continued

```
                180                 185                 190
Val Thr Pro Val Leu Asn Gln Pro Gln Ser Glu Trp Phe Gly Ser Thr
            195                 200                 205

Leu Tyr Asp Gln Val His Pro Asp Asp Val Asp Lys Leu Arg Glu Gln
210                 215                 220

Leu Ser Thr Ser Glu Asn Ala Leu Thr Gly Arg Ile Leu Asp Leu Lys
225                 230                 235                 240

Thr Gly Thr Val Lys Lys Glu Gly Gln Gln Ser Ser Met Arg Met Cys
            245                 250                 255

Met Gly Ser Arg Arg Ser Phe Ile Cys Arg Met Arg Cys Gly Ser Ser
            260                 265                 270

Ser Val Asp Pro Val Ser Val Asn Arg Leu Ser Phe Val Arg Asn Arg
            275                 280                 285

Cys Arg Asn Gly Leu Gly Ser Val Lys Asp Gly Glu Pro His Phe Val
            290                 295                 300

Val Val His Cys Thr Gly Tyr Ile Lys Ala Trp Pro Pro Ala Gly Val
305                 310                 315                 320

Ser Leu Pro Asp Asp Pro Glu Ala Gly Gln Gly Ser Lys Phe Cys
            325                 330                 335

Leu Val Ala Ile Gly Arg Leu Gln Val Thr Ser Ser Pro Asn Cys Thr
            340                 345                 350

Asp Met Ser Asn Val Cys Gln Pro Thr Glu Phe Ile Ser Arg His Asn
            355                 360                 365

Ile Glu Gly Ile Phe Thr Phe Val Asp His Arg Cys Val Ala Thr Val
            370                 375                 380

Gly Tyr Gln Pro Gln Glu Leu Leu Gly Lys Asn Ile Val Glu Phe Cys
385                 390                 395                 400

His Pro Glu Asp Gln Gln Leu Leu Arg Asp Ser Phe Gln Gln Val Val
            405                 410                 415

Lys Leu Lys Gly Gln Val Leu Ser Val Met Phe Arg Phe Arg Ser Lys
            420                 425                 430

Asn Gln Glu Trp Leu Trp Met Arg Thr Ser Ser Phe Thr Phe Gln Asn
            435                 440                 445

Pro Tyr Ser Asp Glu Ile Glu Tyr Ile Ile Cys Thr Asn Thr Asn Val
            450                 455                 460

Lys Asn Ser Ser Gln Glu Pro Arg Pro Thr Leu Ser Asn Thr Ile Gln
465                 470                 475                 480

Arg Pro Gln Leu Gly Pro Thr Ala Asn Leu Pro Leu Glu Met Gly Ser
            485                 490                 495

Gly Gln Leu Ala Pro Arg Gln Gln Gln Gln Thr Glu Leu Asp Met
            500                 505                 510

Val Pro Gly Arg Asp Gly Leu Ala Ser Tyr Asn His Ser Gln Val Val
            515                 520                 525

Gln Pro Val Thr Thr Thr Gly Pro Glu His Ser Lys Pro Leu Glu Lys
            530                 535                 540

Ser Asp Gly Leu Phe Ala Gln Asp Arg Asp Pro Arg Phe Ser Glu Ile
545                 550                 555                 560

Tyr His Asn Ile Asn Ala Asp Gln Ser Lys Gly Ile Ser Ser Ser Thr
            565                 570                 575

Val Pro Ala Thr Gln Gln Leu Phe Ser Gln Gly Asn Thr Phe Pro Pro
            580                 585                 590

Thr Pro Arg Pro Ala Glu Asn Phe Arg Asn Ser Gly Leu Ala Pro Pro
            595                 600                 605
```

-continued

```
Val Thr Ile Val Gln Pro Ser Ala Ser Ala Gly Gln Met Leu Ala Gln
    610                 615                 620

Ile Ser Arg His Ser Asn Pro Thr Gln Gly Ala Thr Pro Thr Trp Thr
625                 630                 635                 640

Pro Thr Thr Arg Ser Gly Phe Ser Ala Gln Gln Val Ala Thr Gln Ala
            645                 650                 655

Thr Ala Lys Thr Arg Thr Ser Gln Phe Gly Val Gly Ser Phe Gln Thr
        660                 665                 670

Pro Ser Ser Phe Ser Ser Met Ser Leu Pro Gly Ala Pro Thr Ala Ser
    675                 680                 685

Pro Gly Ala Ala Ala Tyr Pro Ser Leu Thr Asn Arg Gly Ser Asn Phe
690                 695                 700

Ala Pro Glu Thr Gly Gln Thr Ala Gly Gln Phe Gln Thr Arg Thr Ala
705                 710                 715                 720

Glu Gly Val Gly Val Trp Pro Gln Trp Gln Gly Gln Pro His His
            725                 730                 735

Arg Ser Ser Ser Glu Gln His Val Gln Pro Pro Ala Gln Gln
        740                 745                 750

Pro Gly Gln Pro Glu Val Phe Gln Glu Met Leu Ser Met Leu Gly Asp
    755                 760                 765

Gln Ser Asn Ser Tyr Asn Asn Glu Glu Phe Pro Asp Leu Thr Met Phe
    770                 775                 780

Pro Pro Phe Ser Glu
785

<210> SEQ ID NO 9
<211> LENGTH: 3958
<212> TYPE: DNA
<213> ORGANISM: Homo sapiens

<400> SEQUENCE: 9
gtgctgcctc gtctgagggg acaggaggat caccctcttc gtcgcttcgg ccagtgtgtc      60
gggctgggcc ctgacaagcc acctgaggag aggctcggag ccgggcccgg accccggcga    120
ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240 ctggggccg cccgccgtga agacatcgcg gggaccgatt caccatggag gcgccggcg     300 gcgcgaacga caagaaaaag ataagttctg aacgtcgaaa agaaaagtct cgagatgcag    360
ccagatctcg gcgaagtaaa gaatctgaag ttttttatga gcttgctcat cagttgccac    420
ttccacataa tgtgagttcg catcttgata aggcctctgt gatgaggctt accatcagct    480
atttgcgtgt gaggaaactt ctggatgctg gtgatttgga tattgaagat gacatgaaag    540
cacagatgaa ttgctttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaaatgagag    720
aaatgcttac acacagaaat ggccttgtga aaaagggtaa agaacaaaac acacagcgaa    780
gcttttttct cagaatgaag tgtaccctaa ctagccgagg aagaactatg aacataaagt    840
ctgcaacatg gaaggtattg cactgcacag gccacattca cgtatatgat accaacagta    900
accaacctca gtgtgggtat aagaaaccac ctatgacctg cttggtgctg atttgtgaac    960
ccattcctca cccatcaaat attgaaattc ctttagatag caagacttt ctcagtcgac   1020
```

```
acagcctgga tatgaaattt tcttattgtg atgaaagaat taccgaattg atgggatatg    1080
agccagaaga acttttaggc cgctcaattt atgaatatta tcatgctttg gactctgatc    1140
atctgaccaa aactcatcat gatatgttta ctaaaggaca agtcaccaca ggacagtaca    1200
ggatgcttgc caaaagaggt ggatatgtct gggttgaaac tcaagcaact gtcatatata    1260
acaccaagaa ttctcaacca cagtgcattg tatgtgtgaa ttacgttgtg agtggtatta    1320
ttcagcacga cttgattttc tcccttcaac aaacagaatg tgtccttaaa ccggttgaat    1380
cttcagatat gaaaatgact cagctattca ccaaagttga atcagaagat acaagtagcc    1440
tctttgacaa acttaagaag gaacctgatg ctttaacttt gctggcccca gccgctggag    1500
acacaatcat atctttagat tttggcagca cgacacaga aactgatgac cagcaacttg    1560
aggaagtacc attatataat gatgtaatgc tcccctcacc caacgaaaaa ttacagaata    1620
taaatttggc aatgtctcca ttacccaccg ctgaaacgcc aaagccactt cgaagtagtg    1680
ctgaccctgc actcaatcaa gaagttgcat taaaattaga accaaatcca gagtcactgg    1740
aactttcttt taccatgccc cagattcagg atcagacacc tagtccttcc gatggaagca    1800
ctagacaaag ttcacctgag cctaatagtc ccagtgaata ttgttttat gtggatagtg    1860 atatggtcaa tgaattcaag ttggaattgg tagaaaaact ttttgctgaa gacacagaag    1920
caaagaaccc attttctact caggacacag atttagactt ggagatgtta gctccctata    1980
tcccaatgga tgatgacttc cagttacgtt ccttcgatca gttgtcacca ttagaaagca    2040
gttccgcaag ccctgaaagc gcaagtcctc aaagcacagt tacagtattc cagcagactc    2100
aaatacaaga acctactgct aatgccacca ctaccactgc caccactgat gaattaaaaa    2160
cagtgacaaa agaccgtatg gaagacatta aaatattgat tgcatctcca tctcctaccc    2220
acatacataa agaaactact agtgccacat catcaccata tagagatact caaagtcgga    2280
cagcctcacc aaaacagagca ggaaaaggag tcatagaaca gacagaaaaa tctcatccaa    2340
gaagccctaa cgtgttatct gtcgctttga gtcaaagaac tacagttcct gaggaagaac    2400
taaatccaaa gatactagct ttgcagaatg ctcagagaaa gcgaaaaatg gaacatgatg    2460
gttcactttt tcaagcagta ggaattggaa cattattaca gcagccagac gatcatgcag    2520
ctactacatc actttcttgg aaacgtgtaa aaggatgcaa atctagtgaa cagaatggaa    2580
tggagcaaaa gacaattatt ttaataccct ctgatttagc atgtagactg ctggggcaat    2640
caatggatga aagtggatta ccacagctga ccagttatga ttgtgaagtt aatgctccta    2700
tacaaggcag cagaaaccta ctgcagggtg aagaattact cagagctttg gatcaagtta    2760
actgagcttt tcttaatttt cattcctttt tttggacact ggtggctcac tacctaaagc    2820
agtctattta tattttctac atctaatttt agaagcctgg ctacaatact gcacaaactt    2880
ggttagttca attttgatc ccctttctac ttaatttaca ttaatgctct ttttagtat    2940 gttctttaat gctggatcac agacagctca tttctcagt tttttggtat ttaaaccatt    3000
gcattgcagt agcatcattt taaaaaatgc accttttat ttatttattt ttggctaggg    3060
agtttatccc ttttttcgaat tattttaag aagatgccaa tataatttt gtaagaaggc    3120 agtaaccttt catcatgatc ataggcagtt gaaaaattt tacaccttt tttcacatt    3180 ttacataaat aataatgctt tgccagcagt acgtggtagc cacaattgca caatatattt    3240
tcttaaaaaa taccagcagt tactcatgga atatattctg cgtttataaa actagttttt    3300
aagaagaaat ttttttggc ctatgaaatt gttaaacctg gaacatgaca ttgttaatca    3360
tataataatg attcttaaat gctgtatggt ttattatta aatgggtaaa gccatttaca    3420
```

-continued

```
taatatagaa agatatgcat atatctagaa ggtatgtggc atttatttgg ataaaattct    3480
caattcagag aaatcatctg atgtttctat agtcactttg ccagctcaaa agaaaacaat    3540
accctatgta gttgtggaag tttatgctaa tattgtgtaa ctgatattaa acctaaatgt    3600
tctgcctacc ctgttggtat aaagatattt tgagcagact gtaaacaaga aaaaaaaaat    3660
catgcattct tagcaaaatt gcctagtatg ttaatttgct caaaatacaa tgtttgattt    3720
tatgcacttt gtcgctatta acatcctttt tttcatgtag atttcaataa ttgagtaatt    3780
ttagaagcat tattttagga atatatagtt gtcacagtaa atatcttgtt ttttctatgt    3840
acattgtaca aattttcat tccttttgct ctttgtggtt ggatctaaca ctaactgtat     3900
tgttttgtta catcaaataa acatcttctg tggaccagga aaaaaaaaaa aaaaaaa       3958
```

<210> SEQ ID NO 10
<211> LENGTH: 825
<212> TYPE: PRT
<213> ORGANISM: Homo sapiens

<400> SEQUENCE: 10

```
Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
```

-continued

```
                275                 280                 285
Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
                435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
                515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
                610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
                690                 695                 700
```

```
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
            725                 730                 735
Leu Leu Gln Gln Pro Asp Asp His Ala Ala Thr Thr Ser Leu Ser Trp
        740                 745                 750
Lys Arg Val Lys Gly Cys Lys Ser Ser Glu Gln Asn Gly Met Glu Gln
    755                 760                 765
Lys Thr Ile Ile Leu Ile Pro Ser Asp Leu Ala Cys Arg Leu Leu Gly
    770                 775                 780
Gln Ser Met Asp Glu Ser Gly Leu Pro Gln Leu Thr Ser Tyr Cys Glu
785                 790                 795                 800
Val Asn Ala Pro Ile Gln Gly Ser Arg Asn Leu Leu Gln Gly Glu Glu
                805                 810                 815
Leu Leu Arg Ala Leu Asp Gln Val Asn
            820                 825

<210> SEQ ID NO 11
<211> LENGTH: 3812
<212> TYPE: DNA
<213> ORGANISM: Homo sapiens

<400> SEQUENCE: 11
gtgctgcctc gtctgagggg acaggaggat caccctcttc gtcgcttcgg ccagtgtgtc     60
gggctgggcc ctgacaagcc acctgaggag aggctcggag ccgggcccgg accccggcga    120
ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240
ctggggggccg cccgccgtga agacatcgcg gggaccgatt caccatggag gcgccggcg    300
gcgcgaacga caagaaaaag ataagttctg aacgtcgaaa agaaaagtct cgagatgcag    360
ccagatctcg gcgaagtaaa gaatctgaag ttttttatga gcttgctcat cagttgccac    420
ttccacataa tgtgagttcg catcttgata aggcctctgt gatgaggctt accatcagct    480
atttgcgtgt gaggaaactt ctggatgctg gtgatttgga tattgaagat gacatgaaag    540
cacagatgaa ttgcttttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaaatgagag    720
aaatgcttac acacagaaat ggccttgtga aaaagggtaa agaacaaaac acacagcgaa    780
gcttttttct cagaatgaag tgtaccctaa ctagccgagg aagaactatg aacataaagt    840
ctgcaacatg gaaggtattg cactgcacag gccacattca cgtatatgat accaacagta    900
accaacctca gtgtgggtat aagaaaccac ctatgacctg cttggtgctg atttgtgaac    960
ccattcctca cccatcaaat attgaaattc ctttagatag caagactttc ctcagtcgac   1020
acagcctgga tatgaaattt tcttattgtg atgaaagaat taccgaattg atgggatatg   1080
agccagaaga actttaggc cgctcaattt atgaatatta tcatgctttg gactctgatc   1140
atctgaccaa aactcatcat gatatgttta ctaaaggaca agtcaccaca ggacagtaca   1200
ggatgcttgc caaaagaggt ggatatgtct gggttgaaac tcaagcaact gtcatatata   1260
acaccaagaa ttctcaacca cagtgcattg tatgtgtgaa ttcgttgtg agtggtatta   1320
ttcagcacga cttgatttc tccccttcaac aaacagaatg tgtccttaaa ccggttgaat   1380
```

```
cttcagatat gaaaatgact cagctattca ccaaagttga atcagaagat acaagtagcc    1440
tctttgacaa acttaagaag gaacctgatg ctttaacttt gctggcccca gccgctggag    1500
acacaatcat atctttagat tttggcagca acgacacaga aactgatgac cagcaacttg    1560
aggaagtacc attatataat gatgtaatgc tccoctcacc caacgaaaaa ttacagaata    1620
taaatttggc aatgtctcca ttacccaccg ctgaaacgcc aaagccactt cgaagtagtg    1680
ctgaccctgc actcaatcaa gaagttgcat aaaattaga accaaatcca gagtcactgg    1740
aactttcttt taccatgccc cagattcagg atcagacacc tagtccttcc gatggaagca    1800
ctagacaaag ttcacctgag cctaatagtc ccagtgaata ttgttttat gtggatagtg     1860 atatggtcaa tgaattcaag ttggaattgg tagaaaaact ttttgctgaa gacacagaag    1920
caaagaaccc attttctact caggacacag atttagactt ggagatgtta gctccctata    1980
tcccaatgga tgatgacttc cagttacgtt ccttcgatca gttgtcacca ttagaaagca    2040
gttccgcaag ccctgaaagc gcaagtcctc aaagcacagt tacagtattc cagcagactc    2100
aaatacaaga acctactgct aatgccacca ctaccactgc caccactgat gaattaaaaa    2160
cagtgacaaa agaccgtatg gaagacatta aaatattgat tgcatctcca tctcctaccc    2220
acatacataa agaaactact agtgccacat catcaccata tagagatact caaagtcgga    2280
cagcctcacc aaacagagca ggaaaaggag tcatagaaca gacagaaaaa tctcatccaa    2340
gaagccctaa cgtgttatct gtcgctttga gtcaaagaac tacagttcct gaggaagaac    2400
taaatccaaa gatactagct ttgcagaatg ctcagagaaa gcgaaaaatg gaacatgatg    2460
gttcactttt tcaagcagta ggaattattt agcatgtaga ctgctggggc aatcaatgga    2520
tgaaagtgga ttaccacagc tgaccagtta tgattgtgaa gttaatgctc ctatacaagg    2580
cagcagaaac ctactgcagg gtgaagaatt actcagagct ttggatcaag ttaactgagc    2640 ttttcttaa tttcattcct ttttttggac actggtggct cactacctaa agcagtctat      2700
ttatattttc tacatctaat tttagaagcc tggctacaat actgcacaaa cttggttagt    2760 tcaattttg atcccctttc tacttaattt acattaatgc tcttttttag tatgttcttt       2820
aatgctggat cacagacagc tcattttctc agttttttgg tatttaaacc attgcattgc    2880
agtagcatca ttttaaaaaa tgcacctttt tatttattta tttttggcta gggagtttat    2940 cccttttttcg aattattttt aagaagatgc caatataatt tttgtaagaa ggcagtaacc    3000
tttcatcatg atcataggca gttgaaaaat ttttacacct tttttttcac attttacata    3060
aataataatg ctttgccagc agtacgtggt agccacaatt gcacaatata ttttcttaaa    3120
aaataccagc agttactcat ggaatatatt ctgcgtttat aaaactagtt tttaagaaga    3180
aatttttttt ggcctatgaa attgttaaac ctggaacatg acattgttaa tcatataata    3240
atgattctta aatgctgtat ggtttattat ttaaatgggt aaagccattt acataatata    3300
gaaagatatg catatatcta gaaggtatgt ggcatttatt tggataaaat tctcaattca    3360
gagaaatcat ctgatgtttc tatagtcact ttgccagctc aaaagaaaac aatacccat     3420 gtagttgtgg aagtttatgc taatattgtg taactgatat taaacctaaa tgttctgcct    3480
accctgttgg tataaagata ttttgagcag actgtaaaca agaaaaaaaa aatcatgcat    3540
tcttagcaaa attgcctagt atgttaattt gctcaaaata caatgtttga ttttatgcac    3600
tttgtcgcta ttaacatcct ttttttcatg tagatttcaa taattgagta attttagaag    3660
cattatttta ggaatatata gttgtcacag taaatatctt gttttttcta tgtacattgt    3720
acaaattttt cattccttt gctctttgtg gttggatcta acactaactg tattgttttg      3780
```
ttacatcaaa taaacatctt ctgtggacca gg 3812

<210> SEQ ID NO 12
<211> LENGTH: 735
<212> TYPE: PRT
<213> ORGANISM: Homo sapiens

<400> SEQUENCE: 12

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

```
Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Ile
                725                 730                 735

<210> SEQ ID NO 13
<211> LENGTH: 5186
<212> TYPE: DNA
<213> ORGANISM: Homo sapiens

<400> SEQUENCE: 13
gccacacggg tccggtgccc gctgcgcttc cgccccagcg ctcctgaggc ggccgtacaa      60
```

-continued

```
tcctcggcag tgtcctgaga ctgtatggtc agctcagccc ggcctccgac tccttccgac    120
tcccagcatt cgagccactt tttttttttct ttgaaaactc agaaaagtga ctccttttcc    180
agggaaaaag gaacttgggt tcccttctct ccgtcctctt ttcgggtctg acagcctcca    240
cccactcctt ccccggaccc cgcctccgcg cgcaggttcc tcccagtcac ctttctccac    300
ccccgccccc gcacctagcc cgccgcgcgc caccttccac ctgactgcgc ggggcgctcg    360
ggacctgcgc gcacctcgga ccttcaccac ccgcccgggc gcgggggagc ggacgagggc    420
cacagccccc cacccgccag ggagcccagg tgctcggcgt ctgaacgtct caaagggcca    480
cagcgacaat gacagctgac aaggagaaga aaggagtag ctcggagagg aggaaggaga    540
agtcccggga tgctgcgcgg tgccggcgga gcaaggagac ggaggtgttc tatgagctgg    600
cccatgagct gcctctgccc cacagtgtga gctcccatct ggacaaggcc tccatcatgc    660
gactggcaat cagcttcctg cgaacacaca agctcctctc ctcagtttgc tctgaaaacg    720
agtccgaagc cgaagctgac cagcagatgg acaacttgta cctgaaagcc ttggagggtt    780
tcattgccgt ggtgacccaa gatggcgaca tgatctttct gtcagaaaac atcagcaagt    840
tcatgggact tacacaggtg gagctaacag gacatagtat ctttgacttc actcatccct    900
gcgaccatga ggagattcgt gagaacctga gtctcaaaaa tggctctggt tttgggaaaa    960
aaagcaaaga catgtccaca gagcgggact tcttcatgag gatgaagtgc acggtcacca   1020
acagaggccg tactgtcaac ctcaagtcag ccacctggaa ggtcttgcac tgcacgggcc   1080
aggtgaaagt ctacaacaac tgccctcctc acaatagtct gtgtggctac aaggagcccc   1140
tgctgtcctg cctcatcatc atgtgtgaac caatccagca cccatcccac atggacatcc   1200
ccctggatag caagaccttc ctgagccgcc acagcatgga catgaagttc acctactgtg   1260
atgacagaat cacagaactg attggttacc accctgagga gctgcttggc cgctcagcct   1320
atgaattcta ccatgcgcta gactccgaga acatgaccaa gagtcaccag aacttgtgca   1380
ccaagggtca ggtagtaagt ggccagtacc ggatgctcgc aaagcatggg ggctacgtgt   1440
ggctggagac ccaggggacg gtcatctaca accctcgcaa cctgcagccc cagtgcatca   1500
tgtgtgtcaa ctacgtcctg agtgagattg agaagaatga cgtggtgttc tccatggacc   1560
agactgaatc cctgttcaag cccccacctga tggccatgaa cagcatcttt gatagcagtg   1620
gcaaggggggc tgtgtctgag aagagtaact tcctattcac caagctaaag gaggagcccg   1680
aggagctggc ccagctggct cccacccccag gagacgccat catctctctg gatttcggga   1740
atcagaactt cgaggagtcc tcagcctatg gcaaggccat cctgccccccg agccagccat   1800
gggccacgga gttgaggagc cacagcaccc agagcgaggc tgggagcctg cctgccttca   1860
ccgtgcccca ggcagctgcc ccgggcagca ccaccccccag tgccaccagc agcagcagca   1920
gctgctccac gcccaatagc cctgaagact attacacatc tttggataac gacctgaaga   1980
ttgaagtgat tgagaagctc ttcgccatgg acacagaggc caaggaccaa tgcagtaccc   2040
agacggattt caatgagctg gacttggaga cactggcacc ctatatcccc atggacgggg   2100
aagacttcca gctaagcccc atctgccccg aggagcggct cttggcggag aacccacagt   2160
ccacccccca gcactgcttc agtgccatga caaacattct tccagccactg gcccctgtag   2220
ccccgcacag tcccttcctc ctggacaagt ttcagcagca gctggagagc aagaagacag   2280
agcccgagca ccggcccatg tcctccatct tctttgatgc cggaagcaaa gcatccctgc   2340
caccgtgctg tggccaggcc agcacccctc tctcttccat ggggggcaga tccaataccc   2400
```

```
agtggccccc agatccacca ttacattttg ggcccacaaa gtgggccgtc ggggatcagc   2460
gcacagagtt cttgggagca gcgccgttgg ggcccctgt ctctccaccc catgtctcca    2520
ccttcaagac aaggtctgca aagggttttg gggctcgagg cccagacgtg ctgagtccgg   2580
ccatggtagc cctctccaac aagctgaagc tgaagcgaca gctggagtat gaagagcaag   2640
ccttccagga cctgagcggg ggggacccac ctggtggcag cacctcacat ttgatgtgga   2700
aacggatgaa gaacctcagg ggtgggagct gccctttgat gccggacaag ccactgagcg   2760
caaatgtacc caatgataag ttcacccaaa accccatgag gggcctgggc catcccctga   2820
gacatctgcc gctgccacag cctccatctg ccatcagtcc cggggagaac agcaagagca   2880
ggttcccccc acagtgctac gccacccagt accaggacta cagcctgtcg tcagcccaca   2940
aggtgtcagg catggcaagc cggctgctcg ggccctcatt tgagtcctac ctgctgcccg   3000
aactgaccag atatgactgt gaggtgaacg tgcccgtgct gggaagctcc acgctcctgc   3060
aaggagggga cctcctcaga gccctggacc aggccacctg agccaggcct tctacctggg   3120
cagcacctct gccgacgccg tcccaccagc ttcactctct ccgtctgttt ttgcaactag   3180
gtatttctaa cgccagcaca ctatttacaa gatggactta cctggcagac ttgcccaggt   3240
caccaagcag tggcctttt ctgagatgct cactttatta tccctatttt taaagtacac     3300 aattgttta cctgttctga aatgttctta aattttgtag dattttttc ctccccacct      3360 tcaatgactt ctaatttata ttatccatag gtttctctcc ctccttctcc ttctcacaca    3420
caactgtcca tactaacaag tttggtgcat gtctgttctt ctgtagggag aagctttagc    3480
ttcattttac taaaaagatt cctcgttatt gttgttgcca aagagaaaca aaaatgattt    3540
tgctttccaa gcttggtttg tggcgtctcc ctcgcagagc ccttctcgtt tctttttaa     3600 actaatcacc atattgtaaa tttcagggtt tttttttttt tgtttaagct gactctttgc   3660
tctaattttg gaaaaaaaga aatgtgaagg gtcaactcca acgtatgtgg ttatctgtga    3720
aagttgcaca gcgtggcttt tcctaaactg gtgttttcc cccgcatttg gtggattttt     3780
tattattatt caaaaacata actgagtttt taaaagagg agaaaattta tatctgggtt      3840
aagtgtttat catatatatg ggtactttgt aatatctaaa aacttagaaa cggaaatgga    3900
atcctgctca caaatcact ttaagatctt ttcgaagctg ttaatttttc ttagtgttgt     3960
ggacactgca gacttgtcca gtgctcccac ggcctgtacg gacactgtgg aaggcctccc    4020
tctgtcggct ttttgccatc tgtgatatgc cataggtgtg acaatccgag cagtggagtc    4080
attcagcggg agcactgcgc gctatcccct cacattctct atgtactatg tatgtatgta    4140
ttattattat tgctgccaag agggtctgat ggcacgttgt ggggtcgggg ggtggggcgg    4200
ggaagtgctc taacttttct taaggttttg ttgctagccc ttcaagtgca ctgagctatg    4260
tgactcggat ggtctttcac acggcacatt tggacatttc cagaactacc atgagatggt    4320
ttagacggga attcatgcaa atgagggtc aaaaatggta tagtgacccc gtccacgtcc      4380
tccaagctca cgaccttgga gccccgtgga gctggactga ggaggaggct gcacagcggg    4440
agagcagctg gtccagacca gccctgcagc ccccactcag ccggcagcca gatggccccg    4500
caaggcctcc agggatggcc cctagccaca ggcctgggct gaggtctctg ggtcggtcag    4560
tgacatgtag gtaggaagca ctgaaaatag tgttcccaga gcactttgca actccctggg   4620
taagagggac gacacctctg gttttttcaat accaattaca tggaactttt ctgtaatggg   4680
tacaatgaag aagtttctaa aaacacacac aaagcacatt gggccaacta tttagtaagc    4740
ccggatagac ttattgccaa aaacaaaaaa tagctttcaa aagaaattta agttctatga    4800
```

-continued

```
gaaattcctt agtcatggtg ttgcgtaaat catattttag ctgcacggca ttaccccaca    4860
cagggtggca gaacttgaag ggttactgac gtgtaaatgc tggtatttga tttcctgtgt    4920
gtgttgccct ggcattaagg gcattttacc cttgcagttt tactaaaaca ctgaaaaata    4980
ttccaagctt catattaacc ctacctgtca acgtaacgat ttcatgaacg ttattatatt    5040
gtcgaattcc tactgacaac attataactg tatgggagct taactttata aggaaatgta    5100
ttttgacact ggtatcttat taaagtattc tgatcctaaa aaaaaaaaa aaaaaaaaa     5160 aaaaaaaaa aaaaaaaaaa aaaaaa                                          5186
```

<210> SEQ ID NO 14
<211> LENGTH: 870
<212> TYPE: PRT
<213> ORGANISM: Homo sapiens

<400> SEQUENCE: 14

```
Met Thr Ala Asp Lys Glu Lys Lys Arg Ser Ser Glu Arg Arg Lys
  1               5                  10                  15

Glu Lys Ser Arg Asp Ala Ala Arg Cys Arg Arg Ser Lys Glu Thr Glu
             20                  25                  30

Val Phe Tyr Glu Leu Ala His Glu Leu Pro Leu Pro His Ser Val Ser
         35                  40                  45

Ser His Leu Asp Lys Ala Ser Ile Met Arg Leu Ala Ile Ser Phe Leu
     50                  55                  60

Arg Thr His Lys Leu Leu Ser Ser Val Cys Ser Glu Asn Glu Ser Glu
 65                  70                  75                  80

Ala Glu Ala Asp Gln Gln Met Asp Asn Leu Tyr Leu Lys Ala Leu Glu
                 85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
        115                 120                 125

His Ser Ile Phe Asp Phe Thr His Pro Cys Asp His Glu Glu Ile Arg
    130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175

Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
        195                 200                 205

Asn Ser Leu Cys Gly Tyr Lys Glu Pro Leu Leu Ser Cys Leu Ile Ile
    210                 215                 220

Met Cys Glu Pro Ile Gln His Pro Ser His Met Asp Ile Pro Leu Asp
225                 230                 235                 240

Ser Lys Thr Phe Leu Ser Arg His Ser Met Asp Met Lys Phe Thr Tyr
                245                 250                 255

Cys Asp Asp Arg Ile Thr Glu Leu Ile Gly Tyr His Pro Glu Glu Leu
            260                 265                 270

Leu Gly Arg Ser Ala Tyr Glu Phe Tyr His Ala Leu Asp Ser Glu Asn
        275                 280                 285

Met Thr Lys Ser His Gln Asn Leu Cys Thr Lys Gly Gln Val Val Ser
    290                 295                 300
```

-continued

```
Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
            325                 330                 335

Ile Met Cys Val Asn Tyr Val Leu Ser Glu Ile Glu Lys Asn Asp Val
            340                 345                 350

Val Phe Ser Met Asp Gln Thr Glu Ser Leu Phe Lys Pro His Leu Met
            355                 360                 365

Ala Met Asn Ser Ile Phe Asp Ser Ser Gly Lys Gly Ala Val Ser Glu
            370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
            405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
            435                 440                 445

Ser Glu Ala Gly Ser Leu Pro Ala Phe Thr Val Pro Gln Ala Ala Ala
            450                 455                 460

Pro Gly Ser Thr Thr Pro Ser Ala Thr Ser Ser Ser Ser Cys Ser
465                 470                 475                 480

Thr Pro Asn Ser Pro Glu Asp Tyr Tyr Thr Ser Leu Asp Asn Asp Leu
            485                 490                 495

Lys Ile Glu Val Ile Glu Lys Leu Phe Ala Met Asp Thr Glu Ala Lys
            500                 505                 510

Asp Gln Cys Ser Thr Gln Thr Asp Phe Asn Glu Leu Asp Leu Glu Thr
            515                 520                 525

Leu Ala Pro Tyr Ile Pro Met Asp Gly Glu Asp Phe Gln Leu Ser Pro
            530                 535                 540

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
            565                 570                 575

Val Ala Pro His Ser Pro Phe Leu Leu Asp Lys Phe Gln Gln Gln Leu
            580                 585                 590

Glu Ser Lys Lys Thr Glu Pro Glu His Arg Pro Met Ser Ser Ile Phe
            595                 600                 605

Phe Asp Ala Gly Ser Lys Ala Ser Leu Pro Pro Cys Cys Gly Gln Ala
            610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
            645                 650                 655

Gln Arg Thr Glu Phe Leu Gly Ala Ala Pro Leu Gly Pro Pro Val Ser
            660                 665                 670

Pro Pro His Val Ser Thr Phe Lys Thr Arg Ser Ala Lys Gly Phe Gly
            675                 680                 685

Ala Arg Gly Pro Asp Val Leu Ser Pro Ala Met Val Ala Leu Ser Asn
            690                 695                 700

Lys Leu Lys Leu Lys Arg Gln Leu Glu Tyr Glu Glu Gln Ala Phe Gln
705                 710                 715                 720
```

-continued

```
Asp Leu Ser Gly Gly Asp Pro Pro Gly Gly Ser Thr Ser His Leu Met
            725                 730                 735

Trp Lys Arg Met Lys Asn Leu Arg Gly Gly Ser Cys Pro Leu Met Pro
            740                 745                 750

Asp Lys Pro Leu Ser Ala Asn Val Pro Asn Asp Lys Phe Thr Gln Asn
            755                 760                 765

Pro Met Arg Gly Leu Gly His Pro Leu Arg His Leu Pro Leu Pro Gln
            770                 775                 780

Pro Pro Ser Ala Ile Ser Pro Gly Glu Asn Ser Lys Ser Arg Phe Pro
785                 790                 795                 800

Pro Gln Cys Tyr Ala Thr Gln Tyr Gln Asp Tyr Ser Leu Ser Ser Ala
                805                 810                 815

His Lys Val Ser Gly Met Ala Ser Arg Leu Leu Gly Pro Ser Phe Glu
            820                 825                 830

Ser Tyr Leu Leu Pro Glu Leu Thr Arg Tyr Asp Cys Glu Val Asn Val
            835                 840                 845

Pro Val Leu Gly Ser Ser Thr Leu Leu Gln Gly Gly Asp Leu Leu Arg
850                 855                 860

Ala Leu Asp Gln Ala Thr
865                 870

<210> SEQ ID NO 15
<211> LENGTH: 5827
<212> TYPE: DNA
<213> ORGANISM: Homo sapiens

<400> SEQUENCE: 15
ccgagagcgt gccccggacc gccagctcag aacaggggca gccgtgtagc cgaacggaag        60
ctgggagcag ccgggactgg tggcccgcgc ccgagctccg caggcgggaa gcaccctgga       120
tttaggaagt cccgggagca gcgcggcggc acctccctca cccaaggggc gcggcgacg        180 gtcacgggcg gcggcgccac cgtgagcgac ccaggccagg attctaaata gacggcccag       240
gctcctcctc cgcccgggcc gcctcacctg cgggcattgc cgcgccgcct ccgccggtgt       300
agacggcacc tgcgccgcct tgctcgcggg tctccgcccc tcgcccaccc tcactgcgcc       360
aggcccaggc agctcacctg tactggcgcg ggctgcggaa gctgcgtgaa gccgaggcgt       420
tgaggcgcgg cgcccacgcc actgtcccga gaggacgcag gtggagcggg gcgcggcttcg      480 cggaacccgg cgccggccgc cgcagtggtc ccagcctaca ccgggttccg gggacccggc       540
cgccagtgcc cggggagtag ccgccgccgt cggctgggca ccatgaacag cagcagcgcc       600
aacatcacct acgccagtcg caagcggcgg aagccggtgc agaaaacagt aaagccaatc       660
ccagctgaag gaatcaagtc aaatccttcc aagcggcata gagaccgact taatacagag       720
ttggaccgtt tggctagcct gctgccttc ccacaagatg ttattaataa gttggacaaa       780
ctttcagttc ttaggctcag cgtcagttac ctgagagcca agagcttctt tgatgttgca       840
ttaaaatcct ccctactga agaaacggag gccaggata actgtagagc agcaaattcc       900
agagaaggcc tgaacttaca agaaggagaa ttcttattac aggctctgaa tggctttgta       960
ttagttgtca ctacagatgc tttggtcttt tatgcttctt ctactataca agattatcta      1020
gggtttcagc agtctgatgt catacatcag agtgtatatg aacttatcca taccgaagac      1080
cgagctgaat tcagcgtca gctacactgg gcattaaatc cttctcagtg tacagagtct      1140
ggacaaggaa ttgaagaagc cactggtctc cccccagacag tagtctgtta taacccagac      1200
cagattcctc cagaaaactc tcctttaatg gagaggtgct tcatatgtcg tctaaggtgt      1260
```

```
ctgctggata attcatctgg ttttctggca atgaatttcc aagggaagtt aaagtatctt    1320
catggacaga aaaagaaagg gaaagatgga tcaatacttc cacctcagtt ggctttgttt    1380
gcgatagcta ctccacttca gccaccatcc atacttgaaa tccggaccaa aaattttatc    1440
tttagaacca aacacaaact agacttcaca cctattggtt gtgatgccaa aggaagaatt    1500
gttttaggat atactgaagc agagctgtgc acgagaggct caggttatca gtttattcat    1560
gcagctgata tgctttattg tgccgagtcc catatccgaa tgattaagac tggagaaagt    1620
ggcatgatag ttttccggct tcttacaaaa acaaccgat ggacttgggt ccagtctaat     1680
gcacgcctgc tttataaaaa tggaagacca gattatatca ttgtaactca gagaccacta    1740
acagatgagg aaggaacaga gcatttacga aaacgaaata cgaagttgcc ttttatgttt    1800
accactggag aagctgtgtt gtatgaggca accaacccctt ttcctgccat aatggatccc    1860
ttaccactaa ggactaaaaa tggcactagt ggaaaagact ctgctaccac atccactcta    1920
agcaaggact ctctcaatcc tagttccctc ctggctgcca tgatgcaaca agatgagtct    1980
atttatctct atcctgcttc aagtacttca agtactgcac cttttgaaaa caactttttc    2040
aacgaatcta tgaatgaatg cagaaattgg caagataata ctgcaccgat gggaaatgat    2100
actatcctga acatgagca aattgaccag cctcaggatg tgaactcatt tgctggaggt     2160
cacccagggc tctttcaaga tagtaaaaac agtgacttgt acagcataat gaaaaaccta    2220
ggcattgatt ttgaagacat cagacacatg cagaatgaaa aatttttcag aaatgatttt    2280
tctggtgagg ttgacttcag agacattgac ttaacggatg aaatcctgac gtatgtccaa    2340
gattctttaa gtaagtctcc cttcatacct tcagattatc aacagcaaca gtccttggct    2400
ctgaactcaa gctgtatggt acaggaacac ctacatctag aacagcaaca gcaacatcac    2460
caaaagcaag tagtagtgga gccacagcaa cagctgtgtc agaagatgaa gcacatgcaa    2520
gttaatggca tgtttgaaaa ttggaactct aaccaattcg tgcctttcaa ttgtccacag    2580
caagacccac aacaatataa tgtctttaca gacttacatg ggatcagtca agagttcccc    2640
tacaaatctg aaatggattc tatgccttat acacagaact ttatttcctg taatcagcct    2700
gtattaccac aacattccaa atgtacagag ctggactacc ctatggggag ttttgaacca    2760
tccccatacc ccactacttc tagtttagaa gattttgtca cttgtttaca acttcctgaa    2820
aaccaaaagc atggattaaa tccacagtca gccataataa ctcctcagac atgttatgct    2880
ggggccgtgt cgatgtatca gtgccagcca gaacctcagc acacccacgt gggtcagatg    2940
cagtacaatc cagtactgcc aggccaacag gcatttttaa acaagtttca gaatggagtt    3000
ttaaatgaaa catatccagc tgaattaaat aacataaata cactcagac taccacacat     3060 cttcagccac ttcatcatcc gtcagaagcc agacctttc ctgatttgac atccagtgga     3120
ttcctgtaat tccaagccca atttttgaccc tggttttttgg attaaattag tttgtgaagg    3180
attatggaaa aataaaactg tcactgttgg acgtcagcaa gttcacatgg aggcattgat    3240
gcatgctatt cacaattatt ccaaaccaaa ttttaatttt tgcttttaga aagggagtt     3300 taaaaatggt atcaaaatta catatactac agtcaagata gaaagggtgc tgccacggag    3360
tggtgaggta ccgtctacat ttcacattat tctgggcacc acaaaatata caaaacttta    3420
tcagggaaac taagattctt ttaaattaga aaatattctc tatttgaatt atttctgtca    3480
cagtaaaaat aaaatacttt gagttttgag ctactggatt cttattagtt ccccaaaatac   3540 aaagttagag aactaaacta gttttttccta tcatgttaac ctctgctttt atctcagatg    3600
```

```
ttaaaataaa tggtttggtg cttttttataa aaagataatc tcagtgcttt cctccttcac    3660
tgtttcatct aagtgcctca cattttttc tacctataac actctaggat gtatatttta      3720
tataaagtat tcttttttctt ttttaaatta atatctttct gcacacaaat attatttgtg    3780
tttcctaaat ccaaccattt tcattaattc aggcatattt taactccact gcttacctac    3840
tttcttcagg taaagggcaa ataatgatcg aaaaaataat tatttattac ataatttagt    3900
tgtttctaga ctataaatgt tgctatgtgc cttatgttga aaaaatttaa aagtaaaatg    3960
tctttccaaa ttatttctta attattataa aaatattaag acaatagcac ttaaattcct    4020
caacagtgtt ttcagaagaa ataaatatac cactctttac ctttattgat atctccatga    4080
tgatagttga atgttgcaat gtgaaaaatc tgctgttaac tgcaaccttg tttattaaat    4140
tgcaagaagc tttatttcta gcttttttaat taagcaaagc acccatttca atgtgtataa    4200 attgtctta aaaactgttt tagacctata atccttgata atatattgtg ttgactttat     4260
aaatttcgct tcttagaaca gtggaaacta tgtgttttc tcatatttga ggagtgttaa     4320
gattgcagat agcaaggttt ggtgcaaagt attgtaatga gtgaattgaa tggtgcattg    4380
tatagatata atgaacaaaa ttatttgtaa gatatttgca gttttttcatt ttaaaaagtc   4440 cataccttat atatgcactt aatttgttgg ggctttacat actttatcaa tgtgtctttc    4500
taagaaatca agtaatgaat ccaactgctt aaagttggta ttaataaaaa gacaaccaca    4560
tagttcgttt accttcaaac tttaggtttt tttaatgata tactgatctt cattaccaat    4620
aggcaaatta atcaccctac caactttact gtcctaacat ggtttaaaag aaaaaatgac    4680
accatctttt attctttttt tttttttttt ttgagagaga gtcttactct gccgcccaaa    4740
ctggagtgca gtggcacaat cttggctcac tgcaacctct acctcctggg ttcaagtgat    4800
tctcttgcct cagcctcccg agttgctggg attacaggca tggtggcgtg agcctgtagt    4860
cctagctact caggaggctg aggcaggaga atagcctgaa cctgggaatc ggaggttgca    4920
gagccaagat cgccccactg cactccagcc tggcaataga ccgagactcc gtctccaaaa    4980
aaaaaaaaaa tacaattttt atttcttta ctttttttag taagttaatg tatataaaaa     5040
tggcttcgga caaaatatct ctgagttctg tgtatttca gtcaaaactt taaacctgta    5100
gaatcaattt aagtgttgga aaaaatttgt ctgaaacatt tcataatttg tttccagcat    5160
gaggtatcta aggatttaga ccagaggtct agattaatac tctattttta catttaaacc    5220
ttttattata agtcttacat aaaccatttt tgttactctc ttccacatgt tactggataa    5280
attgtttagt ggaaaatagg ctttttaatc atgaatatga tgacaatcag ttatacagtt    5340
ataaaattaa aagtttgaaa agcaatattg tatattttta tctatataaa ataactaaaa    5400
tgtatctaag aataataaaa tcacgttaaa ccaaatacac gtttgtctgt attgttaagt    5460
gccaaacaaa ggatacttag tgcactgcta cattgtggga tttatttcta gatgatgtgc    5520
acatctaagg atatggatgt gtctaattta gtcttttcct gtaccaggtt tttcttacaa    5580
tacctgaaga cttaccagta ttctagtgta ttatgaagct ttcaacatta ctatgcacaa    5640
actagtgttt ttcgatgtta ctaaatttta ggtaaatgct ttcatggctt ttttcttcaa    5700
aatgttactg cttacatata tcatgcatag attttttgctt aaagtatgat ttataatatc   5760
ctcattatca aagttgtata caataatata taataaaata acaaatatga ataaaaaaaa    5820
aaaaaaa                                                              5827
```

<210> SEQ ID NO 16
<211> LENGTH: 848

```
<212> TYPE: PRT
<213> ORGANISM: Homo sapiens

<400> SEQUENCE: 16

Met Asn Ser Ser Ser Ala Asn Ile Thr Tyr Ala Ser Arg Lys Arg Arg
 1               5                  10                  15

Lys Pro Val Gln Lys Thr Val Lys Pro Ile Pro Ala Glu Gly Ile Lys
             20                  25                  30

Ser Asn Pro Ser Lys Arg His Arg Asp Arg Leu Asn Thr Glu Leu Asp
         35                  40                  45

Arg Leu Ala Ser Leu Leu Pro Phe Pro Gln Asp Val Ile Asn Lys Leu
     50                  55                  60

Asp Lys Leu Ser Val Leu Arg Leu Ser Val Ser Tyr Leu Arg Ala Lys
 65                  70                  75                  80

Ser Phe Phe Asp Val Ala Leu Lys Ser Ser Pro Thr Glu Arg Asn Gly
                 85                  90                  95

Gly Gln Asp Asn Cys Arg Ala Ala Asn Phe Arg Glu Gly Leu Asn Leu
            100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
    130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
            180                 185                 190

Ala Thr Gly Leu Pro Gln Thr Val Val Cys Tyr Asn Pro Asp Gln Ile
        195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
        275                 280                 285

Thr Lys His Lys Leu Asp Phe Thr Pro Ile Gly Cys Asp Ala Lys Gly
    290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400
```

```
Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Gln Ser Leu Ala Leu Asn
        595                 600                 605

Ser Ser Cys Met Val Gln Glu His Leu His Leu Glu Gln Gln Gln Gln
    610                 615                 620

His His Gln Lys Gln Val Val Val Glu Pro Gln Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
            660                 665                 670

Asn Val Phe Thr Asp Leu His Gly Ile Ser Gln Glu Phe Pro Tyr Lys
        675                 680                 685

Ser Glu Met Asp Ser Met Pro Tyr Thr Gln Asn Phe Ile Ser Cys Asn
    690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
            740                 745                 750

Asn Pro Gln Ser Ala Ile Ile Thr Pro Gln Thr Cys Tyr Ala Gly Ala
        755                 760                 765

Val Ser Met Tyr Gln Cys Gln Pro Glu Pro Gln His Thr His Val Gly
    770                 775                 780

Gln Met Gln Tyr Asn Pro Val Leu Pro Gly Gln Ala Phe Leu Asn
785                 790                 795                 800

Lys Phe Gln Asn Gly Val Leu Asn Glu Thr Tyr Pro Ala Glu Leu Asn
                805                 810                 815
```

```
-continued

Asn Ile Asn Asn Thr Gln Thr Thr His Leu Gln Pro Leu His His
            820                 825                 830

Pro Ser Glu Ala Arg Pro Phe Pro Asp Leu Thr Ser Ser Gly Phe Leu
        835                 840                 845
```

METHODS OF TREATING DIABETES

CLAIM OF PRIORITY

This application is a continuation-in-part of International Patent Application PCT/US2005/024866, filed on Jul. 13, 2005, which claims priority under 35 USC §119(e) to U.S. Provisional Patent Application Ser. No. 60/588,071, filed on Jul. 15, 2004, and U.S. Provisional Patent Application Ser. No. 60/624,928, filed on Nov. 4, 2004. This application also claims the benefit of Australian Provisional Patent Application No. 2006/906,499, filed Nov. 21, 2006. The entire contents of all of the foregoing are hereby incorporated by reference.

FEDERALLY SPONSORED RESEARCH OR DEVELOPMENT

This invention was made with Government support under Grant Nos. RO1 DK33201 awarded by the National Institutes of Health, Diabetes Genome Anatomy (DGAP) Grant DK-60837-02 awarded by the National Institute of Diabetes and Digestive and Kidney Diseases of the National Institutes of Health, and the NCRR Islet Cell Resource (RR-016603) awarded by the National Center for Research Resources (NCRR), a component of the National Institutes of Health. The Government has certain rights in the invention.

TECHNICAL FIELD

This invention relates to methods of screening for and treating diabetes-related disorders.

BACKGROUND

The pathogenesis of type 2 diabetes is believed to involve two core defects: insulin resistance and β-cell failure (Martin et al., Lancet, 340:925-929 (1992); Weyer et al., J. Clin. Invest., 104:787-794 (1999); DeFronzo et al., Diabetes Care, 15:318-368 (1992)). Important advances towards the understanding of the development of peripheral insulin resistance have been made in both animal models and humans (Bruning et al., Cell, 88:561-572 (1997); Lauro et al., Nat. Genet., 20:294-298 (1998); Nandi et al., Physiol. Rev., 84:623-647 (2004); Sreekumar et al., Diabetes, 51:1913-1920 (2002); McCarthy and Froguel, Am. J. Physiol. Endocrinol. Metab., 283:E217-E225 (2002); Mauvais-Jarvis and Kahn, Diabetes. Metab., 26:433-448 (2000); Petersen et al., N. Engl. J. Med., 350:664-671 (2004)). However, the mechanisms underlying β-cell failure in humans are less well understood, partly due to difficulty accessing the pancreas, and the small contribution of islets to the total pancreatic mass.

SUMMARY

This invention is based, in part, on the discovery that Aryl hydrocarbon Nuclear Receptor Translocator (ARNT) transcription factor and its binding partners Hypoxia Inducible Factor 1α (HIF1α), HIF2α, and/or the Aryl Hydrocarbon Receptor (AhR) are important for normal glucose handling in pancreatic beta cell function in humans and mice, both in vivo and in vitro. ARNT, HIF1α, HIF2α, and AhR regulate the expression, and thereby the function, of many genes. As described herein, a decrease in levels of one or more of ARNT, HIF1α, HIF2α, and/or AhR in pancreatic beta cells can lead to the development of diabetes-related disorders.

Thus, included herein are methods of screening for compounds that increase levels or activity of one or more of ARNT, HIF1α, HIF2α, and/or AhR, for the treatment and prevention of diabetes-related disorders, including type 1 and type 2 diabetes mellitus, impaired glucose tolerance, insulin resistance and beta cell dysfunction; compounds identified by said screening methods, and methods of using said compounds. Also included are methods for using information regarding the expression, level or activity of one or more of ARNT, HIF1α, HIF2α, and/or AhR in predictive medicine, e.g., diagnostic and prognostic assays, in monitoring clinical trials, and in pharmacogenetics.

In one aspect, the invention provides methods for evaluating a subject for risk, predisposition, or presence of a diabetes-related disorder. The methods include obtaining a sample from the subject; evaluating expression, level or activity of one or more of ARNT, HIF1α, HIF2α, and/or AhR in the sample, and optionally comparing the expression, level, or activity of one or more of ARNT, HIF1α, HIF2α, and/or AhR in the sample to a reference, e.g., a normal control. The expression, level or activity in the sample as compared to the control indicates whether the subject has an increased risk, predisposition, or presence of the diabetes-related disorder. For example, a reference may represent a level in a normal control individual, in an individual who has an increased risk of a diabetes-related disorder, in an individual who has a predisposition to develop a diabetes-related disorder, or an individual who has a diabetes-related disorder. If the level in the subject is less than a reference that represents a level in a normal individual, then the individual has an increased risk of, predisposition to, or has, a diabetes-related disorder. In some embodiments, the method includes assigning a value to said subject for risk, predisposition, or presence of a diabetes-related disorder. In some embodiments, the method further includes providing a record of that value, e.g., to the subject or to a health care provider. In some embodiments, the methods include selecting and administering a treatment for the subject based on the level in the subject.

In some embodiments, the methods include obtaining a sample from the subject; evaluating expression, level, or activity of one or more, e.g., all or a subset (i.e., 1, 2, 3, 4, or more) of the following genes: glucose transporters, e.g., GLUT1 and GLUT3, aldolase-B, glyceraldehyde-3-phosphate dehydrogenase, L-type pyruvate-kinase, and/or genes involved in vascular function and hypoxic response, including vascular endothelial growth factor (VEGF), plasminogen activator inhibitor 1 (PAI1) and erythropoietin (EPO), and optionally comparing the expression, level, or activity of the genes in the sample to a reference, e.g., a normal control. The expression, level or activity in the sample as compared to the control indicates whether the subject has an increased risk, predisposition, or presence of the diabetes-related disorder.

As used herein, a "diabetes-related disorder" includes type 1 diabetes, type 2 diabetes, impaired glucose tolerance, insulin resistance, or beta-cell dysfunction.

In some embodiments, a biological sample from a subject includes cells or tissues from a biopsy, e.g., a pancreatic biopsy. In some embodiments, a biological sample includes a biological fluid, e.g., blood.

A subject can be, e.g., a human or non-human animal, e.g., a non-human mammal.

In some embodiments, evaluating is done by determining one or more of serine phosphorylation levels, protein levels, RNA levels, or gene expression.

In a further aspect, the invention provides methods for treating subjects having or at risk for a diabetes-related disorder. The methods include administering to the subject a therapeutically effective amount of a pharmaceutical composition that increases expression, levels or activity of one or more of ARNT, HIF1α, HIF2α, and/or AhR in the subject, thereby treating the subject. In some embodiments, the pharmaceutical composition comprises one or more of an ARNT, HIF1α, HIF2α, and/or AhR nucleic acid molecule, polypeptide or active fragment thereof, and/or a cell expressing of one or more of an exogenous ARNT, HIF1α, HIF2α, and/or AhR, e.g., a beta cell, e.g., a cell derived from the subject. In some embodiments, the pharmaceutical composition decreases ARNT serine phosphorylation, e.g., comprises okadaic acid.

In another aspect, the invention provides methods of evaluating an effect of a treatment for a diabetes-related disorder. The methods include administering a treatment to the subject; evaluating expression, level or activity of one or more of ARNT, HIF1α, HIF2α, and/or AhR in a sample from the subject after administration of the treatment; and optionally comparing the expression, level or activity of one or more of ARNT, HIF1α, HIF2α, and/or AhR in the sample to a reference value, e.g., a baseline level for the subject, wherein if the expression, level or activity of one or more of ARNT, HIF1α, HIF2α, and/or AhR in the sample has a predetermined relationship to the reference value, e.g., is greater than the value, the treatment has a positive effect on the diabetes-related disorder in the subject. In some embodiments, the methods include assigning a value to said subject for the effectiveness of the treatment for the diabetes-related disorder. In some embodiments, the methods further include providing a record of that value, e.g., to the subject or to a health care provider. In some embodiments, the methods further include determining whether to continue to administer the treatment to the subject, or whether to administer the treatment to another subject. In some embodiments, the methods include evaluating ARNT or HIF1α.

In some embodiments, the methods include evaluating expression, level or activity of ARNT, HIF1α, HIF2α, and/or AhR nucleic acids or polypeptides in a sample from a subject having a diabetes-related disorder before administering the treatment to the subject, to provide a baseline level for the subject. In some embodiments, the methods include evaluating ARNT or HIF1α.

In some embodiments, evaluating the activity of ARNT, HIF1α, HIF2α, and/or AhR is done by a method including analyzing ARNT serine phosphorylation.

In yet another aspect, the invention provides methods for evaluating a compound. In some embodiments, the methods include identifying candidate compounds for the treatment of diabetes-related disorders. The methods include providing a sample comprising one or more of ARNT, HIF1α, HIF2α, and/or AhR, e.g., a cell expressing ARNT, HIF1α, HIF2α, and/or AhR, e.g., a beta cell; contacting the sample with a test compound; and determining if the test compound increases expression, level, or activity of one or more of ARNT, HIF1α, HIF2α, and/or AhR in the sample. A test compound that increases expression, level, or activity of one or more of ARNT, HIF1α, HIF2α, and/or AhR is a candidate compound. In some embodiments, the methods include assigning a value to the test compound for the effectiveness of the test compound in increasing expression, level, or activity of one or more of ARNT, HIF1α, HIF2α, and/or AhR in the sample. In some embodiments, the methods further include identifying the test compound as a candidate compound based on the assigned value.

The invention also provides methods for identifying candidate therapeutic agents for the treatment of a diabetes related disorder. The methods include providing a model of a diabetes-related disorder, e.g., a non-human experimental animal model; contacting the model with a candidate compound that increases expression, level, or activity of one or more of ARNT, HIF1α, HIF2α, and/or AhR identified by a method described herein; and evaluating the effect of the candidate compound on the model. For example, a positive effect on the model, e.g., an improvement in a symptom of an animal model, indicates that the candidate compound is a candidate therapeutic agent for the treatment of a diabetes-related disorder.

Also provided are methods for identifying therapeutic agents for the treatment of diabetes-related disorders. The methods include administering candidate therapeutic agents identified by a methods described herein to a subject having a diabetes-related disorder, and evaluating the effect of the candidate therapeutic agent on a symptom of the disorder. A candidate therapeutic agent that has a positive effect on a symptom of the disorder is a therapeutic agent for the treatment of the diabetes-related disorder.

The invention also provides methods for making pharmaceutical compositions for the treatment of a diabetes-related disorder, by formulating a therapeutic agent identified by a method described herein with a physiologically acceptable carrier.

Also provided herein are pharmaceutical compositions for the treatment of a diabetes-related disorder, including therapeutic agents identified by a method described herein, and physiologically acceptable carriers.

In some embodiments, the test compound is selected from the group consisting of small molecules, polypeptides, and nucleic acids. In some embodiments, the test compound is a cell expressing exogenous one or more of ARNT, HIF1α, HIF2α, and/or AhR, e.g., a beta cell expressing an increased level of one or more of ARNT, HIF1α, HIF2α, and/or AhR. In some embodiments, the test compound is okadaic acid. In some embodiments, the test compound includes one or more of an ARNT, HIF1α, HIF2α, and/or AhR polypeptide or nucleic acid, or an active fragment thereof.

In some embodiments, the test compound improves clearance of dioxins, thereby modulating ARNT expression, level, or activity. In some embodiments, the test compound decreases toxicity of dioxins, thereby modulating ARNT expression, level, or activity.

In some embodiments, determining whether the test compound modulates the activity of one or more of ARNT, HIF1α, HIF2α, and/or AhR includes one or more of analyzing phosphorylation, e.g., serine phosphorylation of ARNT, determining levels of one or both of ARNT and HIF1α polypeptide in the sample, and/or determining levels of a polynucleotide encoding an polypeptide in the sample.

Further, the invention provides methods of treating subjects having diabetes-related disorders, by administering a therapeutically effective amount of a pharmaceutical composition described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3A is a graph of glucose stimulated insulin secretion in female β-ARNT and wild-type mice.

FIG. 3B is a graph of arginine augmentation of glucose stimulated insulin secretion in female β-ARNT and wild-type mice.

DETAILED DESCRIPTION

Figure 1A:
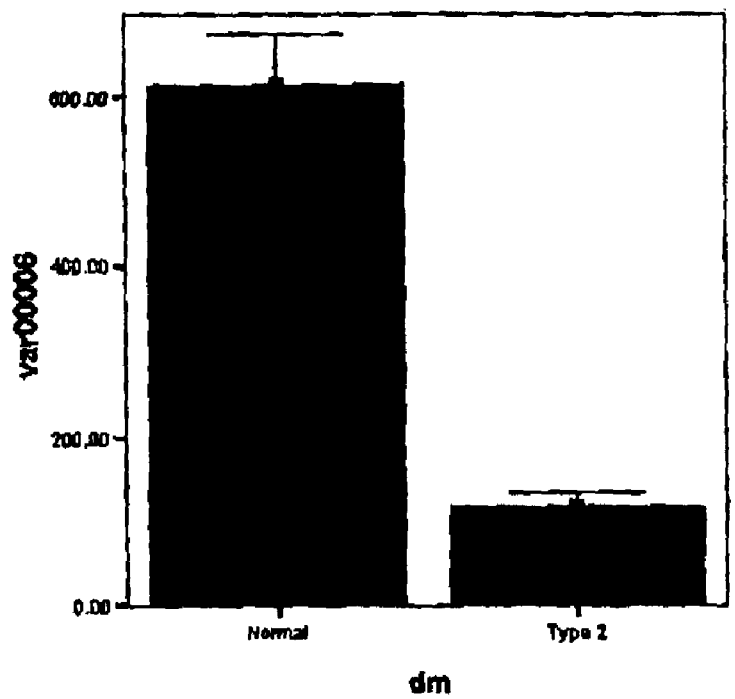
FIG. 1A is a graph of a decrease in ARNT expression in type 2 diabetic subjects, when compared with normal subjects, by microarray analysis.

This invention is based, in part, on the discovery that the aryl hydrocarbon nuclear receptor translocator (ARNT) transcription factor, Hypoxia Inducible Factor 1α (HIF1α), HIF2α, and/or the Aryl Hydrocarbon Receptor (AhR) are important for normal glucose handling in pancreatic beta cell function in humans and mice, both in vivo and in vitro. As described herein, human pancreatic islet samples were obtained from human subjects with type 2 diabetes or normal glucose tolerance. Microarray analysis of those samples demonstrated that both ARNT and HIF1α are significantly downregulated in people with diabetes, and can thus be used as markers of the disease.

ARNT Family Members

ARNT is a member of the basic helix-loop-helix Per/AhR/ARNT/Sim (bHLH-PAS) family of transcription factors. All bHLH-PAS proteins function as obligate dimers. ARNT is absolutely required for the normal function of a number of other bHLH-PAS proteins, including HIF1α, HIF2α, and the aryl hydrocarbon receptor (AhR) (Kozak et al., Dev. Biol., 191:297-305 (1997)). These important transcription factors mediate hypoxic gene regulation (HIF proteins) and response to environmental toxins (AhR). ARNT can also homodimerize and hence activate transcription of genes with E-box promoter elements, however, the physiological relevance of this remains unclear (Antonsson et al., J. Biol. Chem., 270:13968-13972 (1995)). ARNT is essential for normal embryonic development, as demonstrated by the in utero death of knockout mice due to failure of placental vascularisation and accompanying developmental anomalies (Kozak et al., Dev. Biol., 191:297-305 (1997); Abbott and Buckalew, Dev. Dyn., 219:526-538 (2000); Maltepe et al., Nature, 386:403-407 (1997)).

It has been previously reported that ARNT regulates the transcription of a number of genes that may be of interest in diabetes. These include mRNAs coding for proteins involved in glucose metabolism—the glucose transporters GLUT1 and GLUT3, aldolase-B, glyceraldehyde-3-phosphate dehydrogenase and L-type pyruvate-kinase, and genes involved in vascular function and hypoxic response including vascular endothelial growth factor (VEGF), plasminogen activator inhibitor 1 (PAI1) and erythropoietin (EPO) (Zelzer et al., EMBO J., 17:5085-5094 (1998); Salceda et al., Arch. Biochem. Biophys., 334:389-394 (1996); Forsythe et al., Mol. Cell. Biol., 16:4604-4613 (1996); Okino et al., J. Biol. Chem., 273:23837-23843 (1998)).

Sequences useful in the methods described herein include ARNT, HIF1α, HIF2α, and AhR sequences, all of which are known in the art. In some embodiments, the methods include the use of nucleic acids or polypeptides that are at least 80% identical to a human ARNT, HIF1α, HIF2α, or AhR sequence, e.g., at least 80%, 85%, 90%, or 95% identical to a human sequence as described herein.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In the present methods, the percent identity between two amino acid sequences is determined using the Needleman and Wunsch ((1970) J. Mol. Biol. 48:444-453) algorithm which has been incorporated into the GAP program in the GCG software package (available on the world wide web at www.gcg.com), using a Blossum 62 scoring matrix with a gap penalty of 12, a gap extend penalty of 4, and a frameshift gap penalty of 5.

The active fragments of ARNT, HIF1α, HIF2α, and AhR useful in the methods described herein are those that bind to the same DNA sequence (e.g., promoter sequence) that the full-length protein binds to, and has at least 30% of the transcription initiating activity of the full-length protein, e.g., at least 40%, 50%, 60%, 70%, 80%, 90% or more of the activity of the full-length protein, on the same promoters and the same genes as the full-length protein.

Exemplary human ARNT sequences are known in the art and include three splice variants, Genbank Acc. Nos. M69238.1 (complete coding region); NM_001668.2 (isoform 1); NM_178426.1 (isoform 2); and NM_178427.1 (isoform 3). Exemplary non-human ARNT sequences are known in the art and described below. Active fragments of ARNT are DNA binding fragments with transcription activity, and contain one or more of a basic DNA binding sequence, a helix-loop-helix (HLH) dimerization domain, and a PAS region, e.g., PAS A domain, amino acids 177-239 of SEQ ID NO:8; PAS B domain, amino acids 362-458 of SEQ ID NO:8; HLH domain, amino acids 87-143 of SEQ ID NO:8; see also Chapman-Smith et al., J. Biol. Chem., 279 (7):5353-5362 (2003). Methods of identifying active fragments that retain DNA binding activity are known in the art, see, e.g., Chapman-Smith et al., (2003) Id.

Exemplary human HIF1α sequences are known in the art and include isoforms 1 and 2. The mRNA sequence for HIF1α isoform 1 is GenBank Acc. No NM_001530.2 (SEQ ID NO: 9), and the amino acid sequence is Genbank Acc. No. NP_001521.1 (SEQ ID NO:10). Variant 1 encodes the predominant isoform, and is the preferred isoform for use in the methods described herein. The mRNA sequence for HIF1α isoform 2 is Genbank Acc. No. NM_181054.1 (SEQ ID NO:11), and the amino acid sequence is Genbank Acc. No. NP_851397.1 (SEQ ID NO:12). Variant 2 lacks an alternate segment in the 3' CDS, compared to variant 1, that results in a frameshift. The resulting protein (isoform 2) is shorter and has a distinct C-terminus, as compared to isoform 1. Active fragments of HIF1α are DNA binding fragments with transcription activity that include at least one PAS domain, e.g., amino acids 96-150 or 239-338 of SEQ ID NO:10.

HIF2α is also known as Endothelial PAS Domain Protein 1 (EPAS1). Exemplary human HIF2α mRNA sequences are known in the art and include Genbank Acc. No. NM_001430.3 (SEQ ID NO:13), while the amino acid sequence is Genbank Acc. No. NP_001421.2 (SEQ ID NO:14). Active fragments of HIF2α are DNA binding fragments with transcription activity, and contain one or more of a helix loop helix domain at amino acids 22-68 of SEQ ID NO:14; a PAS domain at amino acids 97-147 or 241-340 of SEQ ID NO:14.

Exemplary human AhR mRNA sequences are known in the art and include Genbank Acc. No. NM_001621.3 (SEQ ID NO:15); the amino acid sequence of the protein is SEQ ID NO:16. Active fragments of AhR are DNA binding fragments with transcription activity, and contain at least one PAS region, e.g., amino acids 122-224 or 282-381 of SEQ ID NO:16.

Effects of Knock Out/Knocking Down ARNT, HIF1α, HIF2α, and AhR

ARNT knockout mice die before embryonic day 10 (Kozak et al., Dev. Biol., 191:297-305 (1997); Abbott and Buckalew, Dev. Dyn., 219:526-538 (2000); Maltepe et al., Nature, 386: 403-407 (1997)) due to the failure of placental development. In order to study the effect of deletion of ARNT upon the development of diabetes, β-cell ARNT knockout mice (β-ARNT) were generated using the Cre-lox recombination system. As described herein, these β-ARNT mice develop beta cell dysfunction and diabetes, thus providing a useful model of diabetes related disorders.

In addition, siRNA was used to determine the effect of knocking down HIF1α, HIF2α, and AhR; the results demonstrate that these ARNT family members also play a role, probably in coordination with ARNT.

As described herein, ARNT, HIF1α, HIF2α, and AhR are involved in the development of beta cell dysfunction, impaired glucose tolerance and diabetes. Thus, ARNT, HIF1α, HIF2α, and AhR, singly and in combination, provide new targets for the treatment and prevention of diabetes-related disorders, including type 1 and type 2 diabetes mellitus, impaired glucose tolerance, insulin resistance and beta cell dysfunction.

In addition, methods involving determining the expression, level or activity of ARNT, HIF1α, HIF2α, and AhR as described herein can be used for one or more of the following: a) clinical medicine (e.g., predictive medicine including prognostic assays, diagnostic assays, monitoring clinical trials, selecting subjects for clinical trials, and pharmacogenetics); b) screening assays; and c) methods of treatment (e.g., therapeutic and prophylacetic).

Methods of Identifying a Compound that Modulates Expression, Level or Activity of One or More of ARNT, HIF1α, HIF2α, and AhR A number of methods are known in the art for evaluating whether a compound alters expression, levels or activity of one or more of ARNT, HIF1α, HIF2α, and AhR.

Methods of assessing expression are well known in the art and include, but are not limited to, Northern analysis, ribonuclease protection assay, reverse transcription-polymerase chain reaction (RT-PCR) or RNA in situ hybridization (see, e.g., Sambrook et al., *Molecular Cloning: A Laboratory Manual*, $3^{rd}$ Ed., Cold Spring Harbor Laboratory Press (2001)). Levels of peptides can be monitored by, e.g., Western analysis, immunoassay, or in situ hybridization. Activity, e.g., altered promoter binding and/or transcription activity, can be determined by, e.g., electrophoretic mobility shift assay, DNA footprinting, reporter gene assay, or a serine, threonine, or tyrosine phosphorylation assay. In some embodiments, the effect of a test compound on expression, level or activity is observed as a change in glucose tolerance or insulin secretion of the cell, cell extract, co-culture, explant or subject. In some embodiments, the effect of a test compound on expression, level or activity of one or more of ARNT, HIF1α, HIF2α, and AhR is evaluated in a transgenic cell or non-human animal, or explant, tissue or cell derived therefrom, having altered glucose tolerance or insulin secretion, and can be compared to a control, e.g., wild-type animal, or explant or cell derived therefrom.

The effect of a test compound on expression, level or activity can be evaluated in a cell, e.g., a cultured mammalian cell, a pancreatic beta cell, cell lysate, or subject, e.g., a non-human experimental mammal such as a rodent, e.g., a rat, mouse, or rabbit, or a cell, tissue, or organ explant, e.g., pancreas or pancreatic cells.

In some embodiments, the ability of a test compound to modulate level, expression or activity of one or more of ARNT, HIF1α, HIF2α, and AhR is evaluated in a knockout animal, or other animal having decreased expression, level, or activity of one or more of ARNT, HIF1α, HIF2α, and AhR, such as the ARNT conditional knockout transgenic animal described herein.

In some embodiments, the ability of a test compound to modulate, e.g., increase or decrease, e.g., permanently or temporarily, expression from one or more of an ARNT, HIF1α, HIF2α, and AhR promoter can be evaluated by, e.g., a routine reporter (e.g., LacZ or GFP) transcription assay. For example, a cell or transgenic animal whose genome includes a reporter gene operably linked to an ARNT promoter can be contacted with a test compound; the ability of the test compound to increase or decrease the activity of the reporter gene or gene product is indicative of the ability of the compound to modulate ARNT expression.

The test compound can be administered to a cell, cell extract, explant or subject (e.g., an experimental animal) expressing a transgene comprising an ARNT, HIF1α, HIF2α, or AhR promoter fused to a reporter such as GFP or LacZ (see, e.g., Nehls et al., Science, 272:886-889 (1996), and Lee et al., Dev. Biol., 208:362-374 (1999), describing placing the beta-galactosidase reporter gene under control of the whn promoter). Enhancement or inhibition of transcription of a transgene, e.g., a reporter such as LacZ or GFP, as a result of an effect of the test compound on the promoter or factors regulating transcription from the promoter, can be used to assay an effect of the test compound on transcription of one or more of ARNT, HIF1α, HIF2α, and AhR. Reporter transcript levels, and thus promoter activity, can also be monitored by other known methods, e.g., Northern analysis, ribonuclease protection assay, reverse transcription-polymerase chain reaction (RT-PCR) or RNA in situ hybridization (see, e.g., Cuncliffe et al., Mamm. Genome, 13:245-252 (2002); Sambrook et al., *Molecular Cloning: A Laboratory Manual*, $3^{rd}$ Ed., Cold Spring Harbor Laboratory Press (2001)). Test compounds can also be evaluated using a cell-free system, e.g., an environment including a promoter-reporter transgene (e.g., an ARNT promoter-LacZ transgene), transcription factors binding the promoter, a crude cell lysate or nuclear extract, and one or more test compounds (e.g., a test compound as described herein), wherein an effect of the compound on promoter activity is detected as a color change.

In one embodiment, the screening methods described herein include the use of a chromatin immunoprecipitation (ChIP) CHIP assay, in which cells expressing one or more of ARNT, HIF1α, HIF2α, and AhR, e.g., pancreatic beta cells, are exposed to a test compound. The cells are optionally subjected to crosslinking, e.g., using UV or formaldehyde, to form DNA-protein complexes, and the DNA is fragmented. The DNA-protein complexes are immunoprecipitated, e.g., using an antibody directed to one or more of ARNT, HIF1α, HIF2α, and AhR. The protein is removed (e.g., by enzymatic digestion) and analyzed, e.g., using a microarray. In this way, changes in binding of the transcription factor to its target genes can be evaluated, thus providing a measure of activity of ARNT, HIF1α, HIF2α, or AhR.

Test Compounds

Test compounds for use in the methods described herein are not limited and can include crude or partially or substantially purified extracts of organic sources, e.g., botanical (e.g., herbal) and algal extracts, inorganic elements or compounds, as well as partially or substantially purified or synthetic compounds, e.g., small molecules, polypeptides, antibodies, and polynucleotides, and libraries thereof.

As noted above, ARNT, HIF1α, HIF2α, and AhR are members of the basic helix-loop-helix Per/AhR/ARNT/Sim (bLHL-PAS) family of transcription factors. In some embodiments, the similarities of these proteins can be used to generate computer models of one or more of ARNT, HIF1α, HIF2α, and AhR, to enable the use of rational design methods to identify or create compounds that may interact with one or more of ARNT, HIF1α, HIF2α, and AhR.

A test compound that has been screened by a method described herein and determined to increase expression, levels, or activity of one or more of ARNT, HIF1α, HIF2α, and AhR, can be considered a candidate compound for the treatment of a diabetes-related disorder. A candidate compound that has been screened, e.g., in an in vivo model of a diabetes-related disorder, and determined to have a desirable effect on the disorder, e.g., on one or more symptoms of the disorder, can be considered a candidate therapeutic agent. Candidate therapeutic agents, once screened and verified in a clinical setting, are therapeutic agents. Candidate therapeutic agents and therapeutic agents can be optionally optimized and/or derivatized, and formulated with physiologically acceptable excipients to form pharmaceutical compositions.

Measurement of Glucose Tolerance and Insulin Secretion

Glucose tolerance tests can be performed on animals such as model animals, e.g., animal models of diabetes-related disorders, or on tissues, cells, or humans as described below in the Examples and as known in the art. Glucose-stimulated insulin secretion and arginine-stimulated augmentation of insulin secretion can be analyzed in animals, tissues, cells, or humans e.g., wild-type, transgenic, or knockout, as described below in the Examples, and as known in the art.

Transgenic and Knockout Animals

Methods for generating non-human transgenic or knockout animals are known in the art; described herein and in the Examples below. Such methods typically involve introducing a nucleic acid, e.g., a nucleic acid encoding ARNT, HIF1α, HIF2α, or AhR or a portion thereof, into the germ line of a non-human animal to make a transgenic animal. Exemplary non-human ARNT sequences are known in the art and include, e.g., Genbank Acc. Nos. NM_009709.1 (*Mus musculus*); NM_169254.1 (*Drosophila melanogaster*); NM_012780.1 (*Rattus norvegicus*); and NM_173993.1 (*Bos taurus*); exemplary non-human sequences of HIF1α, HIF2α, and AhR are also known in the art and can be obtained from a public database such as GenBank. Although rodents, e.g., rats, mice, rabbits and guinea pigs, are typically used, other non-human animals can be used. In these methods, typically one or several copies of the nucleic acid are incorporated into the DNA of a mammalian embryo by known transgenic techniques (see, e.g., Nagy et al., *Manipulating the Mouse Embryo: A Laboratory Manual*, $3^{rd}$ Ed., Cold Spring Harbor Laboratory Press (2003)). A protocol for the production of a transgenic rat can be found in Bader et al., Clin. Exp. Pharmacol. Physiol. Suppl., 3:S81-S87 (1996).

Such methods can also involve the use of tissue-specific promoters to generate tissue-specific knockout animals, for example, a pancreatic beta cell-specific knockout of one or more of ARNT, HIF1α, HIF2α, or AhR, driven by an insulin promoter.

The cre-lox system can be used to direct site-specific recombination to create conditional knockout animals, and is described in Orban et al., Proc. Natl. Acad. Sci. USA, 89 (15):6861-6865 (1992); Akagi et al., Nuc. Acids Res., 25 (9):1766-1772 (1997); Lakso et al., Proc. Natl. Acad. Sci. USA, 89:6232-6236 (1992); Rossant and McMahon, Genes Dev., 13 (2):142-145 (1999); Wang et al., Proc. Natl. Acad. Sci. USA, 93:3932-3936 (1996). The Flp-FRT system can also be used to direct site-specific recombination to create conditional transgenic animals, and is described in U.S. Pat. No. 6,774,279; Vooijs et al., Oncogene., 17 (1):1-12 (1998); Ludwig et al., Transgenic Res., 5 (6):385-395 (1996); and Dymecki et al., Dev. Biol., 201 (1):57-65 (1998). Methods for producing transgenic animals can be used to generate an animal, e.g., a mouse, that bears one conditional allele and one wild type allele. Two such heterozygous animals can be crossed to produce offspring that are homozygous for the conditional allele.

For example, in one embodiment, recombinase recognition sequences are introduced into an endogenous ARNT gene of a cell, e.g., a fertilized oocyte or an embryonic stem cell. Such cells can then be used to create non-human transgenic animals in which conditionally regulated ARNT sequences have been introduced into their genome, e.g., homologously recombinant animals in which endogenous ARNT nucleic acid sequences have been rendered conditional. Such animals are useful for studying the function and/or activity of ARNT and for identifying and/or evaluating modulators of ARNT function, as well as the functional consequences of down-regulating or eliminating ARNT activity in an adult animal, e.g., in a tissue-specific manner. Animals in which ARNT has been selectively eliminated from pancreatic beta cells are useful for screening for compounds that can ameliorate the effects of ARNT down regulation.

Transfected or Knockout Cell Lines

Genetically engineered cells, tissues, or animals can be obtained using known methods, e.g., from a cell, e.g., an embryonic stem cell or a pancreatic β cell, in which a nucleic acid of interest, e.g., a nucleic acid which encodes a protein, e.g., one or more of ARNT, HIF1α, HIF2α, and AhR, has been introduced or knocked out. A nucleic acid of interest, or a vector, e.g., a plasmid, including the nucleic acid of interest, can be introduced into a cell, e.g., a prokaryotic or eukaryotic cell, via conventional transformation or transfection techniques, e.g., calcium phosphate or calcium chloride co-precipitation, DEAE-dextran-mediated transfection, lipofection, electroporation or viral infection. Suitable vectors, cells, methods for transforming or transfecting host cells and methods for cloning the nucleic acid of interest into a vector can be found in, e.g., Sambrook et al., *Molecular Cloning: A Laboratory Manual*, $3^{rd}$ Ed., Cold Spring Harbor Laboratory Press (2001).

Gene expression in cells or tissues can also be decreased or abolished by standard methods. For example, small interfering RNA (siRNA) sequences, e.g., directed against one or more of ARNT, HIF1α, HIF2α, and AhR, can be introduced to temporarily decrease or abolish gene expression. Antisense oligonucleotide sequences, e.g., against one or more of ARNT, HIF1α, HIF2α, and AhR gene or RNA, can also be introduced to decrease or abolish gene expression.

Pharmaceutical Compositions and Methods of Administration

The ARNT, HIF1α, HIF2α, or AhR nucleic acids and polypeptides (and active fragments thereof) described herein can be incorporated into pharmaceutical compositions for administration, singly or in combination, to a subject for the treatment or prevention of a disorder described herein. Such compositions typically include the active agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The composition can include a carrier, which can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Therapeutic compounds comprising nucleic acids can be administered by any method suitable for administration of nucleic acid compounds, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88 (2):205-210 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," Current Opinion in Biotechnology 6:698-708 (1995); Weiner, "Liposomes for Protein Delivery: Selecting Manufacture and Development Processes," Immunomethods 4 (3) 201-9 (1994); and Gregoriadis, "Engineering Liposomes for Drug Delivery: Progress and Problems," Trends Biotechnol. 13 (12):527-37 (1995). Mizguchi et al., Cancer Lett. 100:63-69 (1996), describes the use of fusogenic liposomes to deliver a protein, fragment A of diphtheria toxin (DTA), to tumor cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered, e.g., from one or more times per day to one or more times per week; e.g., once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The pharmaceutical compositions can be included in a container, pack, or dispenser together with instructions for administration.

Pharmacokinetic Properties and Therapeutic Activity

In some embodiments, the therapeutic agent is a protein, e.g., a peptide or polypeptide. Modifications can be made to a protein to alter the pharmacokinetic properties of the protein to make it more suitable for use in protein therapy. For example, such modifications can result in longer circulatory half-life, an increase in cellular uptake, improved distribution to targeted tissues, a decrease in clearance and/or a decrease of immunogenicity. A number of approaches useful to optimize the therapeutic activity of a protein, e.g., a therapeutic protein described herein, e.g., one or more of an ARNT, HIF1α, HIF2α, or AhR polypeptide or active fragment thereof, or a protein that modulates expression, level or activity of one or more of ARNT, HIF1α, HIF2α, and AhR, are known in the art, including chemical modification.

Expression System

For recombinant proteins, the choice of expression system can influence pharmacokinetic characteristics. Differences in post-translational processing between expression systems can lead to recombinant proteins of varying molecular size and charge, which can affect circulatory half-life, rate of clearance and immunogenicity, for example. The pharmacokinetic properties of the protein may be optimized by the appropriate selection of an expression system, such as selection of a bacterial, viral, or mammalian expression system. Exemplary mammalian cell lines useful in expression systems for therapeutic proteins are Chinese hamster ovary, (CHO) cells, the monkey COS-1 cell line and the CV-1 cell line.

Chemical Modification

A protein can be chemically altered to enhance the pharmacokinetic properties, while maintaining activity. The protein can be covalently linked to a variety of moieties, altering the molecular size and charge of the protein and consequently its pharmacokinetic characteristics. The moieties are preferably non-toxic and biocompatible. In one embodiment, polyethylene glycol (PEG) can be covalently attached to the protein (PEGylation). A variety of PEG molecules are known and/or commercially available (See, e.g., Sigma-Aldrich catalog). PEGylation can increase the stability of the protein, decrease immunogenicity by steric masking of epitopes, and improve half-life by decreasing glomerular filtration. (See, e.g., Harris and Zalipsky, *Poly(ethylene glycol): Chemistry and Biological Applications*, ACS Symposium Series, No. 680, American Chemical Society (1997); Harris et al., Clinical Pharmacokinetics, 40:7, 485-563 (2001)). Examples of therapeutic proteins administered as PEG constructs include Adagen™ (PEG-ADA) and Oncospar™ (Pegylated asparaginase). In another embodiment, the protein can be similarly linked to oxidized dextrans via an amino group. (See Sheffield, Curr. Drug Targets Cardiovas. Haemat. Dis., 1:1, 1-22 (2001)). In yet another embodiment, conjugation of arginine oligomers to cyclosporin A can facilitates topical delivery (Rothbard et al., Nat. Med., 6 (11):1253-1257 (2000)).

Furthermore, the therapeutic protein can be chemically linked to another protein, e.g., cross-linked (via a bifunctional cross-linking reagent, for example) to a carrier protein to form a larger molecular weight complex with longer circulatory half-life and improved cellular uptake. In some embodiments, the carrier protein can be a serum protein, such as albumin. In another embodiment, the therapeutic protein can cross-link with itself to form a homodimer, a trimer, or a higher analog, e.g., via heterobifunctional or homobifunctional cross-linking reagents (see Stykowski et al., Proc. Natl. Acad. Sci. USA, 95:1184-1188 (1998)). Increasing the molecular weight and size of the therapeutic protein through dimerization or trimerization can decrease clearance.

Modification of Protein Formulation

The formulation of the protein may also be changed. For example, the therapeutic protein can be formulated in a carrier system. The carrier can be a colloidal system. The colloidal system can be a liposome, a phospholipid bilayer vehicle. In one embodiment, the therapeutic protein is encapsulated in a liposome while maintaining protein integrity. As one skilled in the art would appreciate, there are a variety of methods to prepare liposomes. (See Lichtenberg et al., Methods Biochem. Anal., 33:337-462 (1988); Anselem et al., *Liposome Technology*, CRC Press (1993)). Liposomal formulations can delay clearance and increase cellular uptake (See Reddy, Ann. Pharmacother., 34 (7-8):915-923 (2000)).

The carrier can also be a polymer, e.g., a biodegradable, biocompatible polymer matrix. In one embodiment, the therapeutic protein can be embedded in the polymer matrix, while maintaining protein integrity. The polymer may be natural, such as polypeptides, proteins or polysaccharides, or synthetic, such as poly(α-hydroxy) acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, Ann. Pharmacother., 34 (7-8):915-923 (2000)). A polymer formulation for human growth hormone (hGH) has been used in clinical trials. (See Kozarich and Rich, Chemical Biology, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

Gene Therapy

The nucleic acids described herein, e.g., nucleic acids encoding an ARNT, HIF1α, HIF2α, or AhR polypeptide or active fragment thereof, or a nucleic acid encoding a protein that increases expression, level or activity of one or more of ARNT, HIF1α, HIF2α, and AhR, can be incorporated into a gene construct to be used as a part of a gene therapy protocol. The invention includes targeted expression vectors for in vivo transfection and expression of a polynucleotide that encodes an ARNT, HIF1α, HIF2α, or AhR polypeptide or active fragment thereof, or a protein that increases expression, level, or activity of one or more of ARNT, HIF1α, HIF2α, and AhR as described herein, in particular cell types, especially pancreatic beta-cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood, 76:271-278 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., *Current Protocols in Molecular Biology*, Sections 9.10-9.14, Greene Publishing Associates (1989), and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis et al., Science, 230:1395-1398 (1985); Danos and Mulligan, Proc. Natl. Acad. Sci. USA, 85:6460-6464 (1988); Wilson et al., Proc. Natl. Acad. Sci. USA, 85:3014-3018 (1988); Armentano et al., Proc. Natl. Acad. Sci. USA, 87:6141-6145 (1990); Huber et al., Proc. Natl. Acad. Sci. USA, 88:8039-8043 (1991); Ferry et al., Proc. Natl. Acad. Sci. USA, 88:8377-8381 (1991); Chowdhury et al., Science, 254:1802-1805 (1991); van Beusechem et al., Proc. Natl. Acad. Sci. USA, 89:7640-7644 (1992); Kay et al., Human Gene Therapy 3:641-647 (1992); Dai et al., Proc. Natl. Acad. Sci. USA, 89:10892-10895 (1992); Hwu et al., J. Immunol., 150:4104-4115 (1993); U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques, 6:616 (1988); Rosenfeld et al., Science, 252:431-434 (1991); and Rosenfeld et al., Cell, 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., Cell, 68:143-155 (1992)). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., BioTechniques, 6:616 (1988); Haj-Ahmad and Graham, J. Virol., 57:267-274 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol., 158:97-129 (1992)). It is also one of the few viruses that may integrate its DNA into non-dividing cells, and exhibits a high frequency of stable integration (see for example Flotte et al., Am. J. Respir. Cell. Mol. Biol., 7:349-356 (1992); Samulski et al., J. Virol., 63:3822-3828 (1989); and McLaughlin et al., J. Virol., 62:1963-1973

(1989)). Vectors containing as little as 300 base pairs of AAV can be packaged and can integrate. Space for exogenous DNA is limited to about 4.5 kb. An AAV vector such as that described in Tratschin et al., Mol. Cell. Biol., 5:3251-3260 (1985) can be used to introduce DNA into cells. A variety of nucleic acids have been introduced into different cell types using AAV vectors (see for example Hermonat et al., Proc. Natl. Acad. Sci. USA, 81:6466-6470 (1984); Tratschin et al., Mol. Cell. Biol., 4:2072-2081 (1985); Wondisford et al., Mol. Endocrinol., 2:32-39 (1988); Tratschin et al., J. Virol. 51:611-619 (1984); and Flotte et al., J. Biol. Chem. 268:3781-3790 (1993)).

In addition to viral transfer methods, such as those illustrated above, non-viral methods can also be employed to cause expression of a nucleic acid compound described herein (e.g., a nucleic acid encoding an ARNT, HIF1α, HIF2α, or AhR polypeptide or a compound that increases expression, levels or activity of one or more of ARNT, HIF1α, HIF2α; and AhR) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol., 116 (1):131-135 (2001); Cohen et al., Gene Ther., 7 (22): 1896-1905 (2000); or Tam et al., Gene Ther., 7 (21):1867-1874 (2000).

In some embodiments, a gene encoding a compound described herein, e.g., ARNT, HIF1α, HIF2α, or AhR or a compound modulating expression, level or activity of one or more of ARNT, HIF1α, HIF2α, and AhR, is entrapped in liposomes bearing positive charges on their surface (e.g., lipofectins), which can be tagged with antibodies against cell surface antigens of the target tissue (Mizuno et al., No Shinkei Geka, 20:547-551 (1992); PCT publication WO 91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotacetic injection (e.g., Chen et al., Proc. Natl. Acad. Sci. USA 91:3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Cell Therapy

A compound described herein for modulating, e.g., increasing, expression, levels, or activity of one or more of ARNT, HIF1α, HIF2α, and AhR, e.g., an ARNT, HIF1α, HIF2α, or AhR polypeptide or active fragment thereof or a polypeptide from a compound modulating expression, level, or activity of one or more of ARNT, HIF1α, HIF2α, and AhR, can also be increased in a subject by introducing into a cell, e.g., a pancreatic beta cell, a nucleotide sequence that encodes an ARNT, HIF1α, HIF2α, or AhR polypeptide or a polypeptide from a compound modulating expression, level, or activity of one or more of ARNT, HIF1α, HIF2α, and AhR. The nucleotide sequence can be a nucleic acid encoding an ARNT, HIF1α, HIF2α, or AhR or an active fragment thereof, or another polypeptide or peptide that increases activity, levels, or expression of one or more of ARNT, HIF1α, HIF2α, and AhR or an active fragment thereof, and any of: a promoter sequence, e.g., a promoter sequence from an ARNT, HIF1α, HIF2α, or AhR gene or from another gene; an enhancer sequence, e.g., 5' untranslated region (UTR), e.g., a 5' UTR from an ARNT, HIF1α, HIF2α, or AhR gene or from another gene, a 3' UTR, e.g., a 3' UTR from an ARNT, HIF1α, HIF2α, or AhR gene or from another gene; a polyadenylation site; an insulator sequence; or another sequence that increases the expression of one or more of ARNT, HIF1α, HIF2α, and AhR or of a peptide or polypeptide that increases expression, level, or activity of one or more of ARNT, HIF1α, HIF2α, and AhR. The cell can then be introduced into the subject.

Primary and secondary cells to be genetically engineered can be obtained from a variety of tissues and can include cell types that can be maintained and propagated in culture. For example, primary and secondary cells include pancreatic islet β cells, adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells will be administered. However, primary cells may be obtained from a donor (i.e., an individual other than the recipient).

The term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of primary cells which have been passaged one or more times.

Primary or secondary cells of vertebrate, particularly mammalian, origin can be transfected with an exogenous nucleic acid sequence, which includes a nucleic acid sequence encoding a signal peptide, and/or a heterologous nucleic acid sequence, e.g., encoding one or more of ARNT, HIF1α, HIF2α, and AhR, or an agonist or antagonist thereof, and produce the encoded product stably and reproducibly in vitro and in vivo, over extended periods of time.

A heterologous amino acid can also be a regulatory sequence, e.g., a promoter, which causes expression, e.g., inducible expression or upregulation, of an endogenous sequence. An exogenous nucleic acid sequence can be introduced into a primary or a secondary cell by homologous recombination as described, for example, in U.S. Pat. No. 5,641,670, the contents of which are incorporated herein by reference. The transfected primary or secondary cells can also include DNA encoding a selectable marker, which confers a selectable phenotype upon them, facilitating their identification and isolation.

Vertebrate tissue can be obtained by standard methods such a punch biopsy or other surgical methods of obtaining a tissue source of the primary cell type of interest. For example, a biopsy can be used to obtain pancreatic tissue, as a source of islet cells, e.g. beta cells. A mixture of primary cells can be obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly, or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation, all of which are routine in the art.

Transfected primary or secondary cells undergo sufficient numbers of doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Once implanted in an individual, the transfected cells produce the product encoded by the heterologous DNA or are affected by the heterologous DNA itself. For example, an individual who suffers from a diabetes-related disorder (e.g., type 1 diabetes, type 2 diabetes, impaired glucose tolerance, insulin resistance, or beta cell dysfunction) is a candidate for implantation of cells producing an compound described herein, e.g., an ARNT polypeptide or a fragment or analog or mimic thereof or an compound that increases ARNT expression, level, or activity, as described herein.

Diagnostic Assays

The diagnostic assays described herein involve evaluating the ARNT expression, level, or activity in a subject, e.g., in the subject's pancreatic beta cells. Various art-recognized methods are available for evaluating the expression, level, or activity of one or more of ARNT, HIF1α, HIF2α, and AhR. Techniques for detection of expression, level, or activity of one or more of ARNT, HIF1α, HIF2α, and AhR are known in the art and include, inter alia: antibody based assays such as enzyme immunoassays (EIA), radioimmunoassays (RIA), and Western blot analysis. Typically, the level in the subject is compared to the level and/or activity in a control, e.g., the level and/or activity in a tissue from a non-disease subject.

Techniques for evaluating binding activity, e.g., of ARNT to an ARNT binding partner, include fluid phase binding assays, affinity chromatography, size exclusion or gel filtration, ELISA, immunoprecipitation (e.g., the ability of an antibody specific to a first factor, e.g., ARNT, to co-immunoprecipitate a second factor or complex, with which the first factor can associate in nature).

The method can include one or more of the following:

detecting, in a tissue of the subject, the presence or absence of a mutation which affects the expression of a gene encoding ARNT, HIF1α, HIF2α, or AhR, or detecting the presence or absence of a mutation in a region which controls the expression of the gene, e.g., a mutation in the 5' control region;

detecting, in a tissue of the subject, the presence or absence of a mutation which alters the structure of a gene encoding ARNT, HIF1α, HIF2α, or AhR;

detecting, in a tissue of the subject, the misexpression of a gene encoding ARNT, HIF1α, HIF2α, or AhR, at the mRNA level, e.g., detecting a non-wild type level of an mRNA, e.g., a reduced level of an ARNT and/or HIF1αmRNA; and/or detecting, in a tissue of the subject, the misexpression of the gene, at the protein level, e.g., detecting a non-wild type level of an ARNT, HIF1α, HIF2α, or AhR polypeptide, e.g., detecting a reduced level of ARNT and/or HIF1α protein.

In some embodiments the method includes: ascertaining the existence of at least one of: a deletion of one or more nucleotides from a gene encoding ARNT, HIF1α, HIF2α, or AhR; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting a genetic lesion can include: (i) providing a probe/primer including an oligonucleotide containing a region of nucleotide sequence which hybridizes to a sense or antisense sequence from an ARNT, HIF1α, HIF2α, or AhR gene, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

In one embodiment, detecting misexpression includes ascertaining the existence of at least one of: an alteration in the level of a messenger RNA transcript of a gene encoding ARNT, HIF1α, HIF2α, or AhR as compared to a control; the presence of a non-wild type splicing pattern of a messenger RNA transcript of the gene; or a non-wild type level of a gene encoding ARNT, HIF1α, HIF2α, or AhR.

In another embodiment, the method includes determining the structure of a gene encoding ARNT, HIF1α, HIF2α, or AhR, in a subject, an abnormal structure being indicative of risk for the disorder.

In another embodiment, the method includes contacting a sample from the subject with an antibody to a component of the ARNT pathway, such as ARNT, HIF1α, HIF2α, or AhR, or a nucleic acid which hybridizes specifically with the ARNT, HIF1α, HIF2α, or AhR gene.

Expression Monitoring and Profiling.

The expression, level, or activity of ARNT, HIF1α, HIF2α, or AhR (protein or nucleic acid) in a biological sample can be evaluated by obtaining a biological sample from a test subject and contacting the biological sample with a compound or an agent capable of detecting the protein or nucleic acid (e.g., mRNA, genomic DNA) that encodes ARNT, HIF1α, HIF2α, or AhR such that the presence of the protein or nucleic acid is detected in the biological sample. The term biological sample includes tissues, cells and biological fluids isolated from a subject, as well as tissues, cells and fluids present within a subject, e.g., serum, urine, and pancreatic tissue. The expression and level of ARNT, HIF1α, HIF2α, or AhR can be measured in a number of ways, including, but not limited to: measuring the mRNA encoded by the ARNT, HIF1α, HIF2α, or AhR gene; measuring the amount of protein encoded by ARNT, HIF1α, HIF2α, or AhR; or measuring the activity of the protein encoded by the gene.

The level of mRNA corresponding to ARNT, HIF1α, HIF2α, or AhR in a cell can be determined both by in situ and by in vitro formats.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of ARNT, HIF1α, HIF2α, or AhR. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the gene.

The level of mRNA in a sample that is encoded by a gene can be evaluated with nucleic acid amplification, e.g., by rtPCR (U.S. Pat. No. 4,683,202), ligase chain reaction (Barany, Proc. Natl. Acad. Sci. USA, 88:189-193 (1991)), self sustained sequence replication (Guatelli et al., Proc. Natl. Acad. Sci. USA, 87:1874-1878 (1990)), transcriptional amplification system (Kwoh et al., Proc. Natl. Acad. Sci. USA, 86:1173-1177 (1989)), Q-Beta Replicase (Lizardi et al., Bio/Technology, 6:1197 (1988)), rolling circle replication (U.S. Pat. No. 5,854,033) or any other nucleic acid amplification method, followed by the detection of the amplified molecules using techniques known in the art. As used herein, amplification primers are defined as a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further contacting a control sample with a compound or agent capable of detecting mRNA, or genomic DNA, and comparing the presence of the mRNA or genomic DNA in the control sample with the presence of ARNT, HIF1α, HIF2α, or AhR mRNA or genomic DNA in the test sample. In still another embodiment, serial analysis of gene expression, as described in U.S. Pat. No. 5,695,937, is used to detect transcript levels of ARNT, HIF1α, HIF2α, or AhR.

A variety of methods can be used to determine the level of ARNT protein. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect ARNT, HIF1α, HIF2α, or AhR in a biological sample in vitro as well as in vivo. In vitro techniques for detection include enzyme linked immunosorbent assays (ELISAs), immunoprecipitations, immunofluorescence, enzyme immunoassay (EIA), radioimmunoassay (RIA), and Western blot analysis. In vivo techniques for detection include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting ARNT, HIF1α, HIF2α, or AhR, and comparing the presence of one or more of ARNT, HIF1α, HIF2α, and AhR protein in the control sample with the presence of the protein in the test sample.

The invention also includes kits for detecting the presence of one or more of ARNT, HIF1α, HIF2α, and AhR in a biological sample. For example, the kit can include a compound or agent capable of detecting one or more of ARNT, HIF1α, HIF2α, and AhR protein (e.g., an antibody) or mRNA (e.g., a nucleic acid probe); and a standard. The compound or agent can be packaged in a suitable container. The kit can further comprise instructions for using the kit to evaluate a subject, e.g., for risk, predisposition, or presence of a diabetes-related disorder.

The diagnostic methods described herein can identify subjects having, or at risk of developing, diabetes-related disorders, e.g., type 1 diabetes, type 2 diabetes, impaired glucose tolerance, insulin resistance, or beta cell dysfunction. The prognostic assays described herein can be used to determine whether a subject can be administered an compound (e.g., one or more of ARNT, HIF1α, HIF2α, and AhR or an compound modulating level, expression, or activity of one or more of ARNT, HIF1α, HIF2α, and AhR) to treat a diabetes-related disorder.

Kits

A compound or agent as described herein, e.g., an ARNT, HIF1α, HIF2α, or AhR polynucleotide or polypeptide or active fragment thereof, and/or a compound that modulates, e.g., increases, expression, level, or activity of one or more of ARNT, HIF1α, HIF2α, and AhR, can be provided in a kit. The kit can include (a) the agent or compound that modulates expression, level, or activity of one or more of ARNT, HIF1α, HIF2α, and AhR, e.g., a composition that includes an ARNT, HIF1α, HIF2α, or AhR polypeptide or polynucleotide, or an active fragment thereof, and (b) informational material. The informational material can be descriptive, instructional, marketing or other material that relates to the methods described herein and/or the use of the compound or agent in one or more of the methods described herein. For example, the informational material can relate to the diagnosis or treatment of diabetes-related disorders.

Generation of Variants: Production of Altered DNA and Peptide Sequences by Random Methods Amino acid sequence variants of ARNT, HIF1α, HIF2α, or AhR polypeptides or fragments thereof can be prepared by a number of techniques, such as random mutagenesis of DNA that encodes an ARNT, HIF1α, HIF2α, or AhR or a region thereof. Useful methods include PCR mutagenesis and saturation mutagenesis. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., Technique, 1:11-15 (1989)). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Myers et al., Science, 229:242-247 (1985)). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA Tetrahedron, 39:3 (1983); Itakura et al., Recombinant DNA, *Proc 3rd Cleveland Sympos. Macromolecules*, ed. A G Walton, Amsterdam: Elsevier, 273-289 (1981); Itakura et al., Annu. Rev. Biochem., 53:323 (1984); Itakura et al., Science, 198:1056 (1984); Ike et al., Nucleic Acid Res., 11:477 (1983). Such techniques have been employed in the directed evolution of other proteins (see, for example, Scott et al., Science, 249:386-390 (1990); Roberts et al., Proc. Natl. Acad. Sci. USA, 89:2429-2433 (1992); Devlin et al., Science, 249: 404-406 (1990); Cwirla et al., Proc. Natl. Acad. Sci. USA, 87: 6378-6382 (1990); as well as U.S. Pat. Nos. 5,223,409, 5,198, 346, and 5,096,815).

Generation of Variants: Production of Altered DNA and Peptide Sequences by Directed Mutagenesis Non-random or directed mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, (Cunningham and Wells, Science, 244:1081-1085 (1989)). In alanine scanning, a residue or group of target residues are identified (e.g., charged residues such as Arg, Asp, H is, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA (see, e.g., Adelman et al., DNA 2:183 (1983)). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., Proc. Natl. Acad. Sci. USA, 75:5765 (1978).

Cassette Mutagenesis

Another method for preparing variants, cassette mutagenesis, is based on the technique described by Wells et al., Gene, 34:315 (1985). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate variants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, e.g., small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with one or more of ARNT, HIF1α, HIF2α, and AhR. These can include, e.g., agonists, superagonists, and antagonists of ARNT, HIF1α, HIF2α, or AhR (the subject protein and a protein it interacts with are used as the bait protein and fish proteins). These assays rely on detecting the reconstitution of a functional transcriptional activator mediated by protein-protein interactions with a bait protein. In particular, these assays make use of chimeric genes that express hybrid proteins. The first hybrid comprises a DNA-binding domain fused to the bait protein, e.g., ARNT, HIF1α, HIF2α, or AhR or active fragments thereof. The second hybrid protein contains a transcriptional activation domain fused to a fish protein, e.g., an expression library. If the fish and bait proteins are able to interact, they bring into close proximity the DNA-binding and transcriptional activator domains. This proximity is sufficient to cause transcription of a reporter gene, which is operably linked to a transcriptional regulatory site, which is recognized by the DNA binding domain; and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay." For example, the gene library can be cloned into the gene for a surface membrane protein of a bacterial cell, and the resulting fusion protein detected by panning (Ladner et al., WO 88/06630; Fuchs et al., Bio/Technology, 9:1370-1371 (1991); and Goward et al., TIBS, 18:136-140 (1992)). This technique was used in Sahu et al., J. Immunology, 157:884-891 (1996), to isolate a complement inhibitor. In a similar fashion, a detectably labeled ligand can be used to score for potentially functional peptide homologs. Fluorescently labeled ligands, e.g., receptors, can be used to detect homologs that retain ligand-binding activity. The use of fluorescently labeled ligands allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phage M13, fd., and fl are most often used in phage display libraries. Either of the phage gIII or gVIII coat proteins can be used to generate fusion proteins, without disrupting the ultimate packaging of the viral particle. Foreign epitopes can be expressed at the $NH_2$-terminal end of pIII and phage bearing such epitopes recovered from a large excess of phage lacking this epitope (Ladner et al., PCT publication WO 90/02909; Garrard et al., PCT publication WO 92/09690; Marks et al., J. Biol. Chem., 267:16007-16010 (1992); Griffiths et al., EMBO J., 12:725-734 (1993); Clackson et al., Nature, 352:624-628 (1991); and Barbas et al., Proc. Natl. Acad. Sci. USA, 89:4457-4461 (1992)).

A common approach uses the maltose receptor of *E. coli* (the outer membrane protein, LamB) as a peptide fusion partner (Charbit et al., EMBO, 5:3029-3037 (1986)). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al., Vaccines, 91:387-392 (1991)), PhoE (Agterberg et al., Gene, 88:37-45 (1990)), and PAL (Fuchs et al., Bio/Tech., 9:1369-1372 (1991)), as well as large bacterial surface structures have served as vehicles for peptide display. Peptides can be fused to pilin, a protein which polymerizes to form the pilus-a conduit for interbacterial exchange of genetic information (Thiry et al., Appl. Environ. Microbiol., 55:984-993 (1989)). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al., Bio/Tech., 6:1080-1083 (1988)). Surface proteins of other bacterial species have also served as peptide fusion partners. Examples include the *Staphylococcus* protein A and the outer membrane protease IgA of *Neisseria* (Hansson et al., J. Bacteriol., 174:4239-4245 (1992) and Klauser et al., EMBO J., 9:1991-1999 (1990)).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al., Proc. Natl. Acad. Sci. USA, 89:1865-1869 (1992)). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al., Proc. Natl. Acad. Sci. USA, 89:1869 (1992))

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al., Proc. Natl. Acad. Sci. USA, 87:6378-6382 (1990)) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al., J. Med. Chem., 37 (9):1233-1251 (1994)). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al., J. Med. Chem., 37 (9):1233-1251 (1994)), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes can be cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret et al., Anal. Biochem., 204: 357-364 (1992)). To identify the sequences of the active peptides one sequences the DNA produced by the phagemid host.

Secondary Screens

The high through-put assays described above can be followed (or substituted) by secondary screens in order to identify biological activities which will, e.g., allow one skilled in the art to differentiate agonists from antagonists. The type of a secondary screen used will depend on the desired activity that needs to be tested. For example, glucose tolerance and insulin secretion assays described herein can be used, in which the ability to modulate, e.g., decrease or increase or mimic expression, level, or activity of one or more of ARNT, HIF1α, HIF2α, and AhR in pancreatic islet beta cells can be used to identify agonists and antagonists of ARNT, HIF1α, HIF2α, or AhR from a group of peptide fragments isolated though one of the primary screens described above.

Peptide Mimetics

The invention also provides for production of the protein binding domains of ARNT, HIF1α, HIF2α, or AhR, to generate mimetics, e.g. peptide or non-peptide agents, e.g., agonists.

Non-hydrolyzable peptide analogs of critical residues can be generated using benzodiazepine (e.g., see Freidinger et al., in *Peptides: Chemistry and Biology*, Marshall ed., ESCOM Publisher: Leiden, Netherlands (1988)), azepine (e.g., see Huffman et al., in *Peptides: Chemistry and Biology*, G. R. Marshall ed., ESCOM Publisher: Leiden, Netherlands (1988)), substituted gamma lactam rings (Garvey et al., in *Peptides: Chemistry and Biology*, G. R. Marshall ed., ESCOM Publisher: Leiden, Netherlands (1988)), keto-methylene pseudopeptides (Ewenson et al., J. Med. Chem., 29:295 (1986); and Ewenson et al., in *Peptides: Structure and Function* (Proceedings of the 9th American Peptide Symposium) Pierce Chemical Co. Rockland, Ill. (1985)), β-turn dipeptide cores (Nagai et al., Tetrahedron Lett. 26:647 (1985); and Sato et al., J. Chem. Soc. Perkin. Trans., 1:1231 (1986)), and b-aminoalcohols (Gordon et al., Biochem. Biophys. Res. Commun., 126:419 (1985); and Dann et al., Biochem. Biophys. Res. Commun., 134:71 (1986)).

The invention is further described in the following examples, which do not limit the scope of the invention described in the claims.

EXAMPLES

Example 1

ARNT mRNA Expression is Decreased in Type 2 Diabetic Subjects

To identify candidate genes for the development of type 2 diabetes in humans, we isolated pancreatic islets were isolated from subjects with and without type 2 diabetes and the resulting cRNA was subjected to oligonucleotide microarray analysis.

Isolated islets were purified from 5 type 2 diabetic subjects and 7 normoglycemic controls using the modified Ricordi method (Ricordi et al., Diabetes, 37:413-420 (1988)). Demographic characteristics of the humans from whom islets were isolated are shown in Table 1 below. Average age was 47 years in both groups. The mean duration of Type 2 diabetes was 5.8±2.1 years, and no subjects were insulin-requiring. Mean HbA1c was 7.5±0.5% in the diabetic subjects.

All subjects had suffered catastrophic intra-cerebral events. The subjects with type 2 diabetes were all within 10 years of diagnosis, and none were routinely insulin-treated. The normal subjects maintained serum glucose >7.0 mmol/L without insulin treatment. The control subjects were available for islet isolation because they were unsuitable as donors for whole pancreas transplantation, due to previous pancreatic/biliary surgery, vascular disease and/or obesity. Additional clinical information is not available, as the subjects were participants in organ donation programs.

There was no difference in islet yield, islet purity or islet viability between groups. Purity of islets was assessed by dithizone staining, with mean purity estimated at >80%. Islet purification was also assessed by using an Affymetrix microarray to examinine expression of 13 genes that have been reported to best differentiate pancreatic endocrine from exocrine tissues (Cras-Meneur et al., Diabetologia, 47:284-299 (2004)). None of these genes differed between the two patient groups. Expression of the pancreatic hormones preproinsulin, glucagon, somatostatin, and pancreatic polypeptide (PP) did not differ significantly between the diabetic and normal glucose tolerant groups. By array, expression of preproinsulin was 186000 in the diabetic group. The median array expression was 1500, indicating the expected very high level of preproinsulin expression in islets. Expression of a number of important islet transcription factors, including MafA, Nkx2.2, Nkx6.1, NGN3, Notch/HES1, and PAX4, did not differ significantly in diabetic islets as determined by Affymetrix microarray analysis. There were trends towards increased expression of Foxa2/HNF3β (p=0.06) and Pax4 (p=0.06).

Islet viability was >90% as assessed by standard fluorescent inclusion and exclusion dyes. RNA was extracted from at least 1000 islets per subject, and no samples were pooled. RNA was isolated as described in Yechoor et al., Proc. Natl. Acad. Sci. USA, 99:10587-10592 (2002). cRNA was prepared from >8 μg of RNA per subject as described (Yechoor et al., Proc. Natl. Acad. Sci. USA, 99:10587-10592 (2002)) and hybridized to Affymetrix U133A and B microarrays (for a total of 24 arrays). Data from the Affymetrix microarrays were normalized as previously described (Yechoor et al., Proc. Natl. Acad. Sci. USA, 99:10587-10592 (2002)).

1779 cDNA/ESTs represented on the arrays differed at the p<0.05 level, 370 at the p<0.01 level and 65 at the p<0.001 level. Of genes differing at the p<0.05 level, 56.7% were increased and 43.3% were decreased in the diabetic cohort. RT-PCR was performed as previously described with specific primers for each of the genes. Every experiment included a control gene (TATA-box binding protein (TBP), transthyretin and/or 18S RNA, none of which differed significantly). RT-PCR results were tested for significance using Student's unpaired T-test.

Figure 1B:
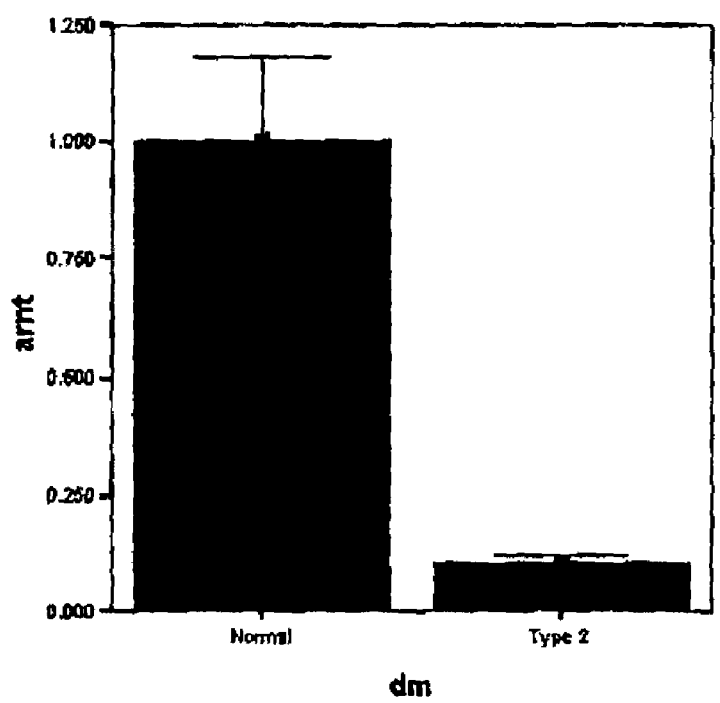
FIG. 1B is a graph of a decrease in mRNA ARNT in type 2 diabetic subjects, when compared with normal subjects, by real-time polymerase chain reaction analysis.

The most significantly down-regulated gene in islets from humans with type 2 diabetes was ARNT (18.2% of control, p=0.000012). Microarray analysis showed that ARNT expression was undetectable in 5 out of 5 diabetic subjects, versus detectable in 7 of 7 people with normal glucose tolerance (FIG. 1A, p=0.000012). Real-time polymerase chain reaction confirmed that the mRNA for ARNT was substantially and significantly decreased in human islets from type 2 diabetics, to 10.2% of control (p=$2.5 \times 10^{-9}$) (FIG. 1B).

In addition, HIF1α, HIF2α and AhR were all expressed in the human islets. HIF1α was significantly decreased in human islets isolated from people with type 2 diabetes (>90% decrease, p<0.001).

The results of the above study suggest that ARNT is involved in the development or progression of Type 2 diabetes.

TABLE 1

Characteristics of the normal and diabetic subjects from whom islets were isolated.

|  | Control (7) | Diabetes (5) |
|---|---|---|
| Sex (F/M) | 5/2 | 5/0 |
| Age (years) | 47.7 ± 13.5 | 47.5 ± 7.9 |
| Weight (kg) | 98 ± 31 | 65 ± 7 |
| Height (m) | 1.67 ± 0.07 | 1.56 ± 0.05 * |
| BMI (kg/m²) | 30.9 ± 8.6 | 26.6 ± 0.9 |
| Caucasian ethnicity | 6 | 4 |

BMI = body mass index, ± indicates ± 1SD.
* = p = 0.03.

Example 2

Generation of β-Cell Specific ARNT Knockout (β-ARNT) Mice and Islet Immunohistochemistry Whole-body ARNT knockout mice die before embryonic day 10 (Abbott and Buckalew, Dev. Dyn., 219:526-538 (2000); Kozak et al., Dev. Biol., 191:297-305 (1997); Maltepe et al., Nature, 386:403-407 (1997)). In order to study the effect of deletion of ARNT on the development of diabetes, β-cell specific ARNT knockout (β-ARNT) mice were generated using the Cre-lox recombination system. Two lox-p sites were inserted into the ARNT gene as previously described (Tomita et al., Mol. Endocrinol., 14:1674-1681 (2000)). Homozygous lox/lox mice were interbred with mice expressing Cre-recombinase under control of the rat insulin promoter (RIP-Cre), which were a kind gift from Dr. Mark Magnuson. This breeding resulted in mice with β-cell deletion of ARNT (β-ARNT) and floxed wild-type littermates. β-ARNT mice were born at the expected frequencies, were fertile and did not differ significantly in weight or length.

Example 3

Figure 2:
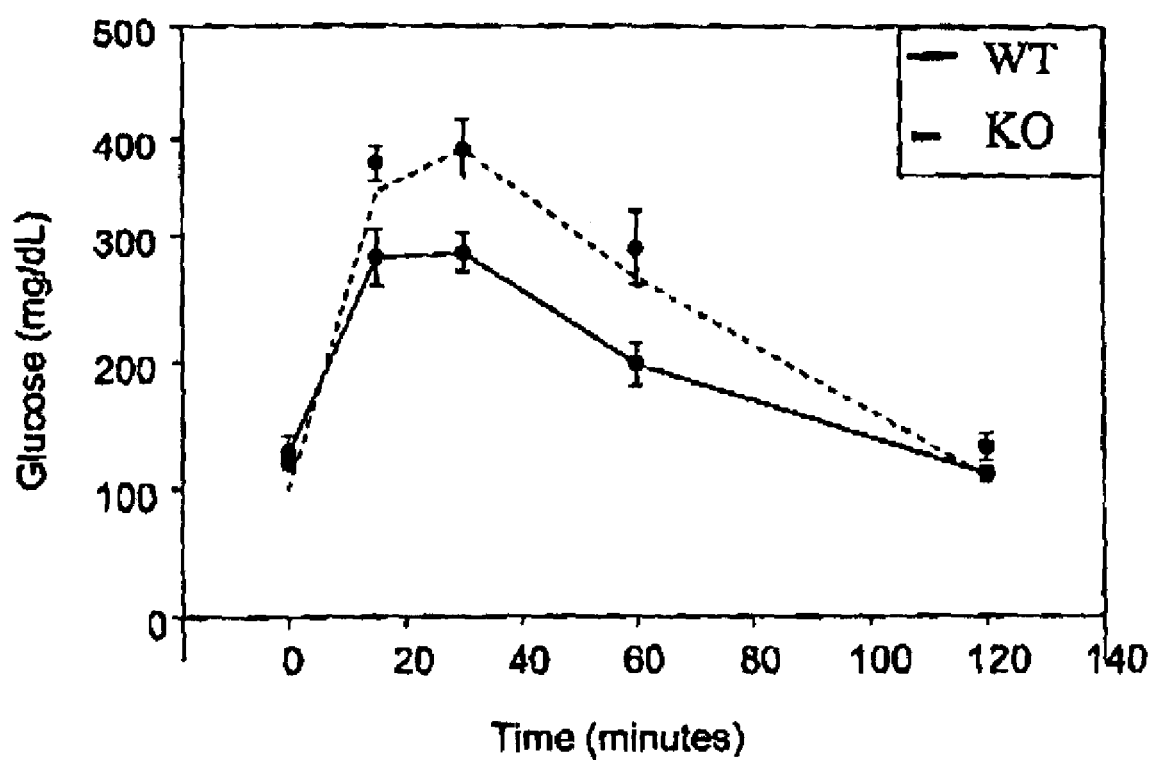
FIG. 2 is a graph of glucose tolerance testing of wild-type female mice and female mice with β-cell specific ARNT deletion (β-ARNT).

Female β-ARNT KO Mice Show Higher Serum Glucose Levels During Glucose Tolerance Testing To examine the role of ARNT in diabetes, glucose tolerance tests were performed after overnight fasting in knockout β-ARNT mice and their wild-type littermates at 9-11 weeks of age, using 1 or 2 g/kg of intraperitoneal (IP) glucose. Blood was collected in the random-fed state for glucose, insulin and leptin levels.

β-ARNT female mice showed significantly higher serum glucose during glucose tolerance testing than wild-type littermates as shown in FIG. 2A ($p<0.01$ by ANOVA for repeated measures). Male β-ARNT mice, however, did not differ from male wild-type mice, either at 9-11 weeks of age or at 8 months of age. Random-fed glucose levels did not differ significantly between knockout and wild-type mice.

Therefore, lack of ARNT in β cells of female mice contributed to the development of symptoms of diabetes.

Example 4

Female β-ARNT Mice Show Abolished Insulin Secretion Following Glucose or Arginine Stimulation Insulin secretion was analyzed in β-ARNT mice in order to further explore the role of ARNT in the development and progression of diabetes.

Glucose-stimulated insulin secretion was assessed following IP injection of 3 g/kg of glucose (Kulkarni et al., Cell, 96:329-339 (1999)). Arginine-stimulated augmentation of insulin secretion was studied following IP injection of 3 g/kg of glucose plus 0.3 mg/kg of arginine (Kulkarni et al., Cell, 96:329-339 (1999)). Insulin was measured using an ELISA kit (Crystal Chem, Chicago, Ill.).

Female β-ARNT mice had fasting insulin levels similar to those in wild-type mice, but glucose stimulation of insulin secretion in response to IP glucose injection was totally abolished (FIG. 3A, $p<0.01$ versus WT). Male mice had a normal response to glucose and did not differ significantly from WT controls. Consistent with the results following glucose stimulation, female β-ARNT mice had no augmentation of insulin secretion after arginine stimulation, and in fact no significant rise in insulin concentration at all (FIG. 3B, $p<0.01$ versus WT). Wild-type mice clearly displayed augmentation with arginine ($p<0.01$ versus glucose alone). Male knockout mice did not differ significantly from wild-type littermates.

These results indicate that ARNT is involved in the pathways leading to insulin secretion, necessary after glucose stimulation.

Example 5

Islets from β-ARNT Knockout Mice Display Defective Glucose-Stimulated Insulin Release and Altered mRNA Expression To determine the basis of the defect in glucose stimulated insulin secretion in the β-ARNT mice, islets from β-ARNT and control animals were examined.

Pancreatic islets were isolated from mice aged 10-12 weeks, as previously described (Kulkarni et al., Cell, 96:329-339 (1999)). Islet isolation was performed blinded to genotype to avoid bias in islet selection for secretion studies. The total number of islets isolated from β-ARNT and control mice did not differ. Equal numbers of islets were subjected to stimulation of insulin secretion at glucose concentrations of 3.3, 5.5, 8.3, 11 and 25 mM. The remaining islets were reserved for RNA isolation and quantitative real-time-PCR.

Figure 3C:
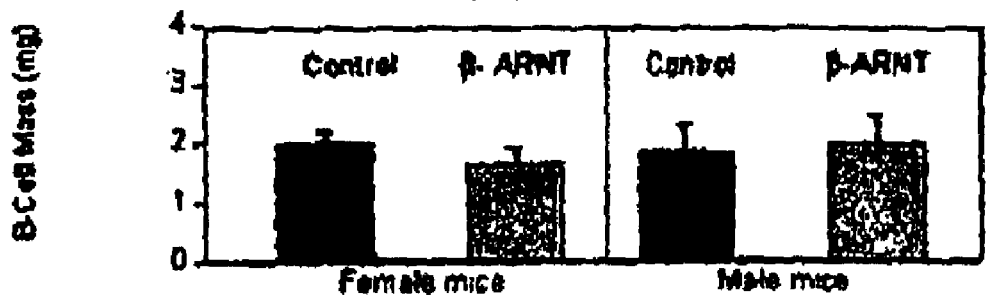
FIG. 3C is a pair of bar graphs illustrating beta cell mass; there was no significant difference between β-ARNT knockout mice and controls, for either males or females.
Figure 3D:
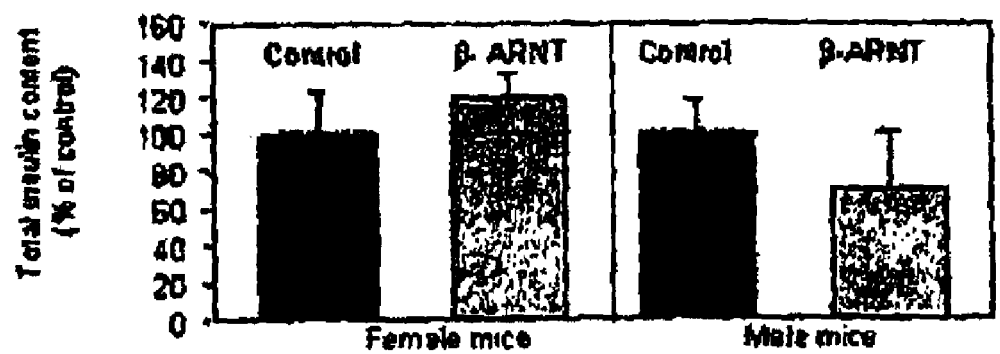
FIG. 3D is a pair of bar graphs showing that total insulin content also did not differ between β-ARNT and control mice either for female or male mice.
Figure 3E:
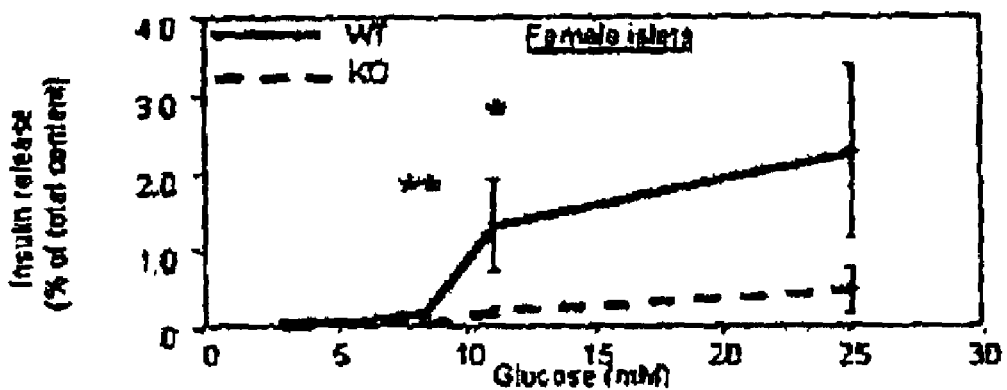
FIG. 3E is a line graph illustrating insulin release from female β-ARNT islets, which was significantly lower at glucose concentrations of 8.3 and 11 mM, and showed a trend towards lower secretion at 25 mM glucose. $*p<0.05$. Error bars are ±1 SEM.
Figure 3F:
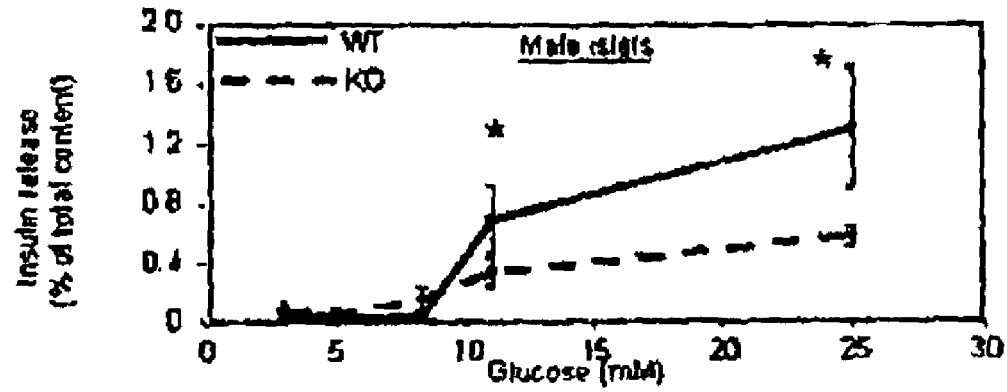
FIG. 3F is a line graph illustrating insulin release from β-ARNT islets from male mice, which was also significantly lower than from flox-control islets, at glucose concentrations of 11 and 25 mM. $*p<0.05$, $**p<0.01$. Error bars are ±1 SEM.

Isolated islets were stained with a cocktail for insulin, DAPI and ARNT as described in Kulkarni et al., J. Clin. Invest., 104:R69-R75 (1999). The results indicated that ARNT deletion was highly effective in the knockout mice.

β-cell mass was examined by an observer blinded to mouse genotype, and did not differ between β-ARNT and control mice (FIG. 3C). Islet isolation gave similar yields of 227±19 and 236±12 islets in β-ARNT and control mice, respectively. Total insulin content did not differ between β-ARNT and control mice for either female or male mice (FIG. 3D). Using islets from either females or males, insulin release was low and equal at low glucose concentrations (3 or 5 mM). However, at glucose concentrations of 8.3 and 11 mM, insulin release from female β-ARNT islets was significantly lower than in controls ($p<0.01$ and $p<0.05$, respectively) (FIG. 3E). This trend continued at 25 mM glucose, but the difference did not achieve statistical significance at this high glucose level. In male β-ARNT mice, insulin release was also lower, at both 11 and 25 mM glucose (FIG. 3F).

Figure 3G:
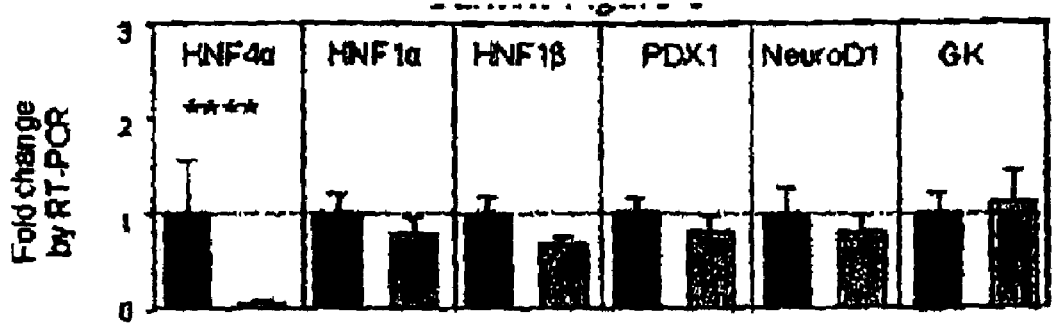
FIG. 3G is a panel of six bar graphs illustrating MODY genes' mRNA expression, determined by real-time PCR in β-ARNT KO and control mouse islets. HNF4α was highly significantly decreased in β-ARNT KO islets (grey bars) compared to floxed controls (black bars). $****p<0.0001$. Error bars are ±1 SEM.
Figure 3H:
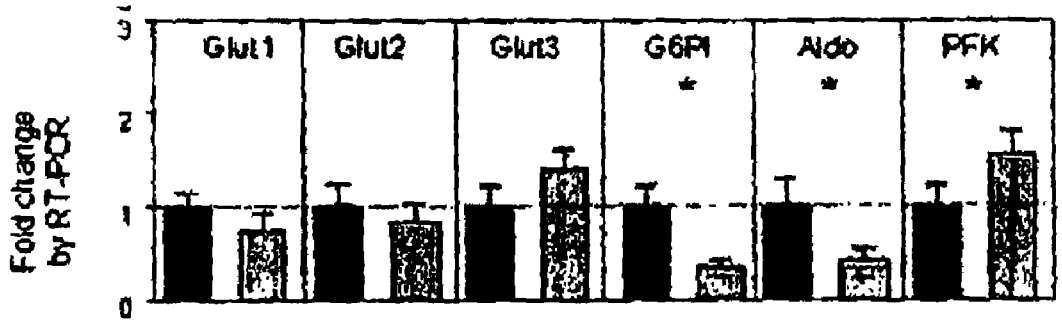
FIG. 3H is a panel of six bar graphs illustrating mRNA expression for six glucose uptake and metabolism genes, determined by real-time PCR in β-ARNT KO and control mouse islets. glucose-6-phospho-isomerase (G6PI) and Aldolase (Aldo) were significantly decreased in β-ARNT KO islets (grey bars) compared to floxed controls (black bars). Phosphofructokinase (PFK) expression was significantly increased in β-ARNT KO islets. $*p<0.05$. Error bars are ±1 SEM.
Figure 3I:
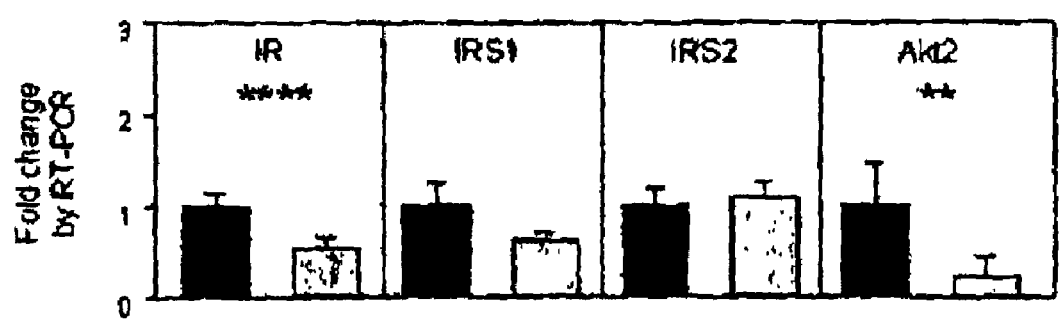
FIG. 3I is a panel of four bar graphs showing that insulin receptor and Akt2 gene expression were significantly decreased in islets from β-ARNT KO islets (grey bars) compared to floxed controls (black bars), as determined by real-time PCR. $p<0.01$, $**p<0.0001$. Error bars are ±1 SEM.
Figure 3J:
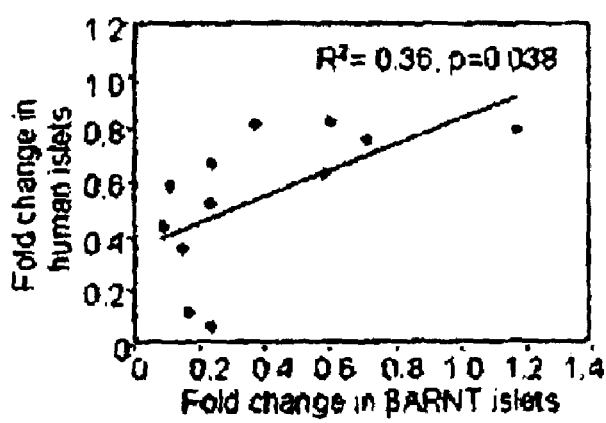
FIG. 3J is graph showing a significant correlation between the fold change in mRNA expression in type-2 human islets and the fold change in the islets of the β-ARNT mice (r2=0.36, p=0.038).

RNA was isolated from the remaining islets and analyzed by real-time PCR. The results for male and female mice did not differ significantly, so are presented together. As shown in FIG. 3G, of the genes associated with MODY in humans, HNF4α was substantially and significantly decreased (92% decrease, $p<0.0001$). Expression of glucose transporters GLUT1 and GLUT2 were not altered. However, glucose-6-phosphoisomerase and aldolase were significantly decreased (46%, $p=0.044$ and 54%, $p=0.048$ respectively) (FIG. 3H). Insulin receptor expression was decreased by 46% ($p<0.0001$), and there was a 73% decrease in Akt2 expression ($p=0.007$) (FIG. 3I). Again, the changes observed in mRNA expression in β-ARNT islets paralleled those seen in human pancreatic islets and those in Min6 cells treated with siRNA to decrease ARNT. The fold change of gene expression in human type 2 islets plotted against fold-change in βARNT mouse islets is shown in FIG. 3J for genes with a putative ARNT-binding site in the first 2 KB of their promoter regions, and was significant ($r_2=0.36$, $p=0.038$). Interestingly, for the mRNAs examined, the results for male and female mice did not differ significantly, suggesting that the ability of male mice to maintain near normal glucose tolerance and insulin secretion depends on compensation by some other component of the insulin secretion or insulin action pathway.

Among potential ARNT partners, expression of mRNAs for AhR, BMAL1, HIF1α, and HIF2α/EPAS1 were clearly detectable in mouse islets.

Example 6

Comparison to Other Mouse Models of Diabetes

To evaluate ARNT function in other mouse models of diabetes, RNA was isolated from islets of 3 other mouse models of islet dysfunction and diabetes: ob/ob mice, db/db mice and β-cell-specific insulin receptor knockout mice (βIRKO), all at 10-12 weeks of age. The first two models have hyperglycemia (456-464 mg/dl versus 195-286 mg/dl), while βIRKO mice are normoglycemic (197±18 versus 187±33 mg/dl in controls), as expected at this young age.

Briefly, pancreatic islets were isolated from ob/ob mice, db/db mice, β-cell specific insulin-receptor knockout mice, and their appropriate controls (obc, dbc, and IR-lox mice) at 10-12 weeks of age. RNA was isolated using standard methods and used for real-time PCR to examine gene expression of ARNT.

Figure 3K:
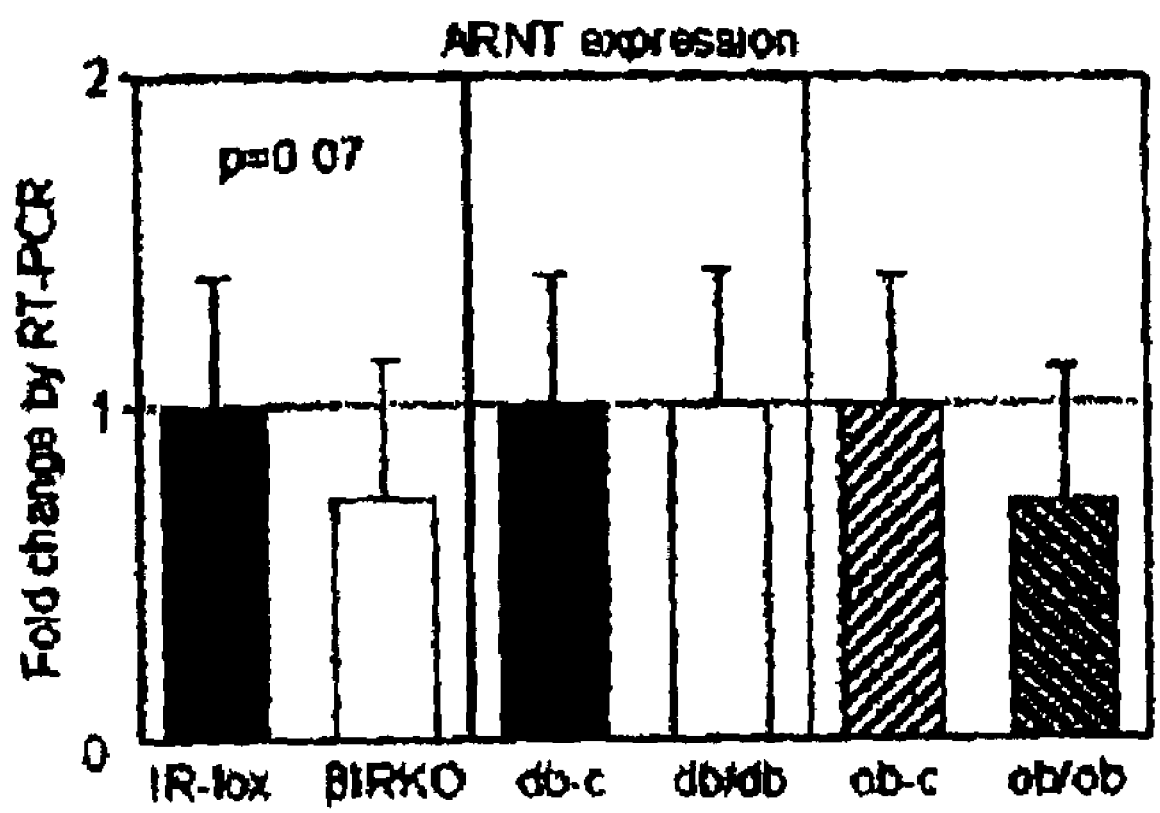
FIG. 3K is a panel of three bar graphs showing levels of ARNT expression in islets isolated from other mouse models of diabetes (IR-lox mice and β-cell specific insulin receptor knockout (βIRKO), ob control (ob-c) and ob/ob, db control (db-c) and db/db), as determined by real-time PCR.

There was a trend towards decreased ARNT expression in βIRKO mice (74% of expression in IR-lox animals, p=0.07), and no significant change in ARNT expression in db/db or ob/ob mice (FIG. 3K).

These results suggest that the substantial decrease in ARNT in human islets is not likely to be mediated solely by diabetes, hyperglycemia or insulin resistance.

Example 7

Decreasing ARNT Expression with the Use of Small Interfering RNA (siRNA) in Vitro Results in an Impairment of Glucose-Stimulated Insulin Secretion In order to study the effects of ARNT in vitro, ARNT expression was decreased in a cell line using small interfering RNA (siRNA).

Min6 cells, a glucose-responsive β-cell line, were treated with a number of different siRNA molecules directed against ARNT, smartpool siRNA (Dharmacon) directed against ARNT for 48 hours. Scrambled sequence siRNA was used as a control in all experiments. Following siRNA treatment, ARNT protein was assessed by Western immunoblot after separation of 100 μg of total protein by 10% SDS-PAGE, using a monoclonal anti-ARNT antibody (BD Biosciences). Glucose stimulated insulin secretion was assessed in triplicate well in 3 separate experiments. In a separate experiment, treated cells were lysed and RNA isolated for RT-PCR.

Figure 4A:
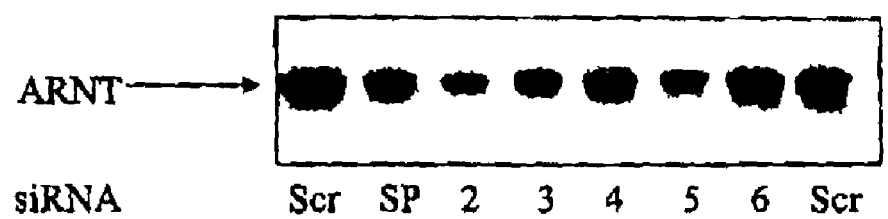
FIG. 4A is a Western blot of ARNT expression in Min6 cells, following treatment with six different small interfering RNAs (siRNAs) or with scrambled controls.
Figure 4B:
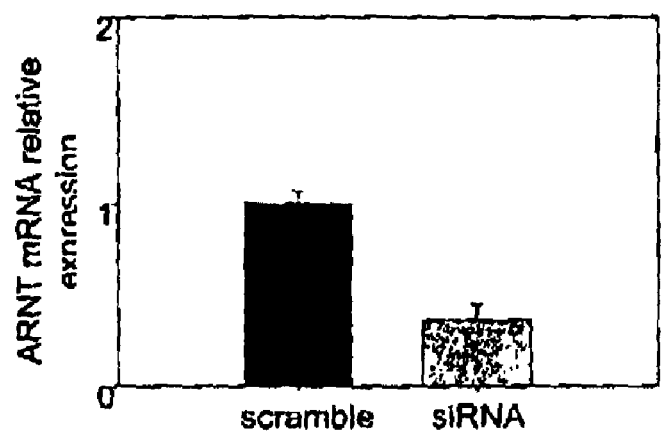
FIG. 4B is a bar graph of ARNT mRNA expression, following treatment with siRNA.
Figure 4C:
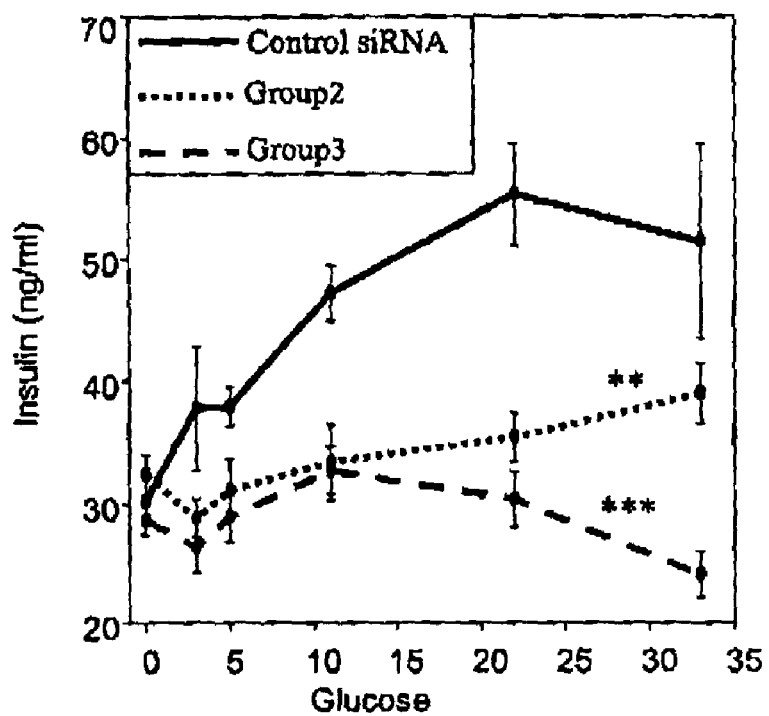
FIG. 4C is a line graph of glucose stimulated insulin secretion by Min6 cells treated with three groups of siRNAs.

As shown in FIG. 4A, siRNA treatments decreased ARNT protein, with varying levels of effectiveness. ARNT mRNA was also decreased (FIG. 4B). The siRNAs were grouped, as follows: controls were placed in group 1, siRNAs 1, 3, 4, and 6, which resulted in a moderate decrease (about 40%) in ARNT, were placed in group 2, and siRNAs 2 and 5, which were the most effective (a decrease of >80%), were placed in group 3. As shown in FIG. 4C, decreasing ARNT by siRNA in group 2 severely impaired glucose-stimulated insulin secretion (a decrease of about 50%, p<0.01 by ANOVA for repeated measures) and siRNA in group 3 substantially abolished glucose-stimulated insulin secretion (p<0.001 by ANOVA for repeated measures).

Thus, decreasing ARNT expression in vitro also leads to the development of diabetes-like symptoms, confirming our in vivo data.

TABLE 2

| siRNA No. | siRNA sequences Sequence | SEQ ID NO: |
|---|---|---|
| 1 | AAGUGGAGGAGCUGUUGUACA | 1 |
| 2 | AAGCGACGGAACAAGAUGACA | 2 |
| 3 | AAAGGCUGCAGGUAACUAGUU | 3 |
| 4 | AAGACCAACAACUUCUAAGAG | 4 |

TABLE 2-continued

| siRNA No. | siRNA sequences Sequence | SEQ ID NO: |
|---|---|---|
| 5 | AAGCACACAGAACUGGAUAUG | 5 |
| 6 | AACCUUCAGUGCUAUGUCUCU | 6 |

Example 8

Decreasing ARNT Expression with the Use of Small Interfering RNA (siRNA) Leads to a Decrease in the Expression of a Number of Genes The effect of a decrease in ARNT expression on the expression of other genes involved in diabetes-related disorders was analyzed using siRNA and real-time PCR.

Figure 5A:
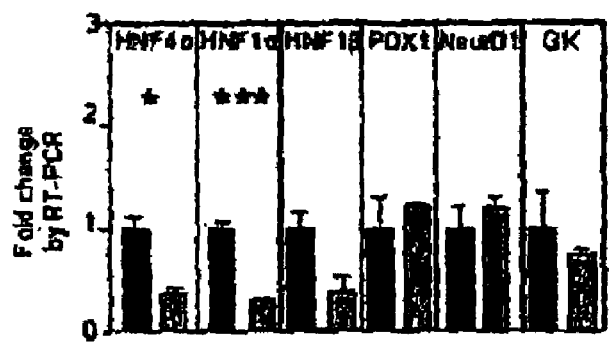
FIG. 5A is a panel of six bar graphs showing changes in mRNA levels for MODY genes (analyzed by real-time PCR), following ARNT siRNA treatment of Min6 cells. Among the MODY genes, decreased ARNT was associated with significantly decreased HNF4α and HNF1α. Black bars, scrambled control siRNA; grey bars, active ARNT siRNA. $*=<0.05$, $=P<0.01$ versus control, $*=p<0.001$, $††=p<0.01$ versus control at 0 mM glucose, $‡‡<0.01$ versus ARNT siRNA 30 mM glucose. Error bars are ±1 SEM.
Figure 5B:
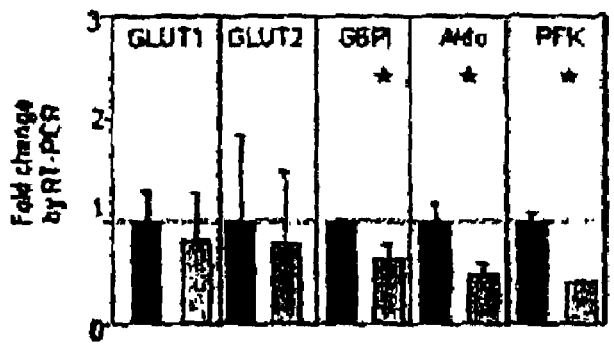
FIG. 5B is a panel of five bar graphs showing changes in mRNA levels for glucose uptake and metabolism genes, analyzed by real-time PCR, following ARNT siRNA treatment of Min6 cells. Expression of glucose-6-phosphoisomerase (G6PI), Aldolase (Aldo) and phosphofructokinase (PFK) were significantly decreased following siRNA treatment. Black bars, scrambled control siRNA; grey bars, active ARNT siRNA. $*=p<0.05$, $=p<0.01$ versus control, $*=p<0.001$, $††=p<0.01$ versus control at 0 mM glucose, $‡‡=p<0.01$ versus ARNT siRNA 30 mM glucose. Error bars are ±1 SEM.
Figure 5C:
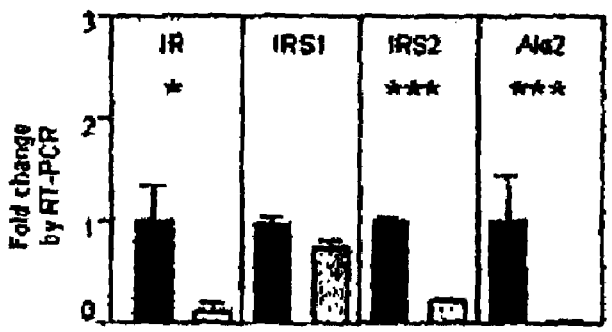
FIG. 5C is a panel of four bar graphs showing changes in mRNA levels analyzed by real-time PCR, following ARNT siRNA treatment of Min6 cells. siRNA treatment led to decreased expression of insulin receptor (IR), insulin receptor substrate 2 (IRS2) and Akt2. $*=p<0.05$, $=p<0.01$ versus control, $*=p<0.001$, $††=p<0.01$ versus control at 0 mM glucose, $‡‡=p<0.01$ versus ARNT siRNA 30 mM glucose. Error bars are ±1 SEM.

RNA was isolated from Min6 cells treated with siRNA 2 directed against ARNT or control scrambled siRNA for real-time PCR. Real-time-PCR of RNA isolated from Min6 cells revealed that siRNA treatment also led to significant decreases in the expression of HNF4α (60% decrease, p=0.012) and HNF1α (68% decrease, p<0.0001) (FIG. 5A), glucose-6-phosphoisomerase (35% decrease, p=0.039), aldolase (50% decrease, p=0.048) and phosphofructokinase (59% decrease, p=0.047) (FIG. 5B), insulin receptor (88% decrease, p=0.044), IRS-2 (78% decrease, p<0.001), and Akt2 (97% decrease, p<0.0001) (FIG. 5C). Aldolase has been previously reported to be regulated by ARNT (Zelzer et al., EMBO J., 17:5085-5094 (1998); Salceda et al., Arch. Biochem. Biophys., 334:389-394 (1996)).

Together, these marked changes in gene expression would be expected to impair β-cell function, glucose metabolism, and glucose-responsive insulin secretion, which was seen in FIG. 4F.

Figure 5D:
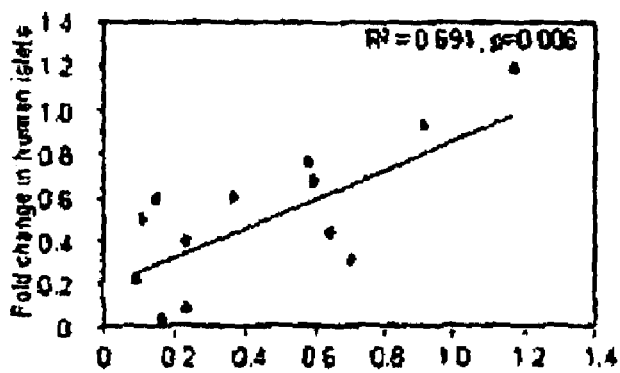
FIG. 5D is a line graph showing that, for genes with a potential ARNT-binding site in the promoter, the fold change in mRNA expression in type-2 human islets was correlated with the fold-change in siRNA treated Min6 cells, $r^2=0.69$.

The changes in mRNA expression in the Min6 cells with reduced ARNT expression closely paralleled the changes observed in the human islets from people with type 2 diabetes. When the real-time PCR fold-changes were plotted against each other, there was a strong and highly significant correlation between the change in type 2 islets and the change in siRNA treated Min6 cells for genes with a putative ARNT-binding site in the first 2 KB of their promoter regions ($r^2$=0.69 and p=0.006, FIG. 5D).

Example 9

Figure 5E:
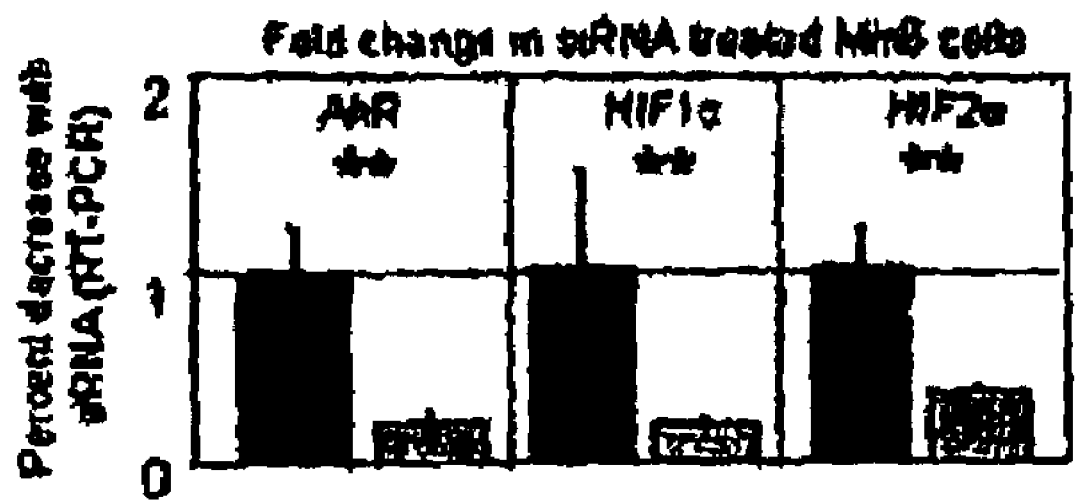
FIG. 5E is a panel of three bar graphs illustrating expression leveles in Min6 cells were treated with RNAi directed against HIF1α, HIF2α, AhR or ARNT for 48 hours. These caused >65% decreases in mRNA expression.
Figure 5F:
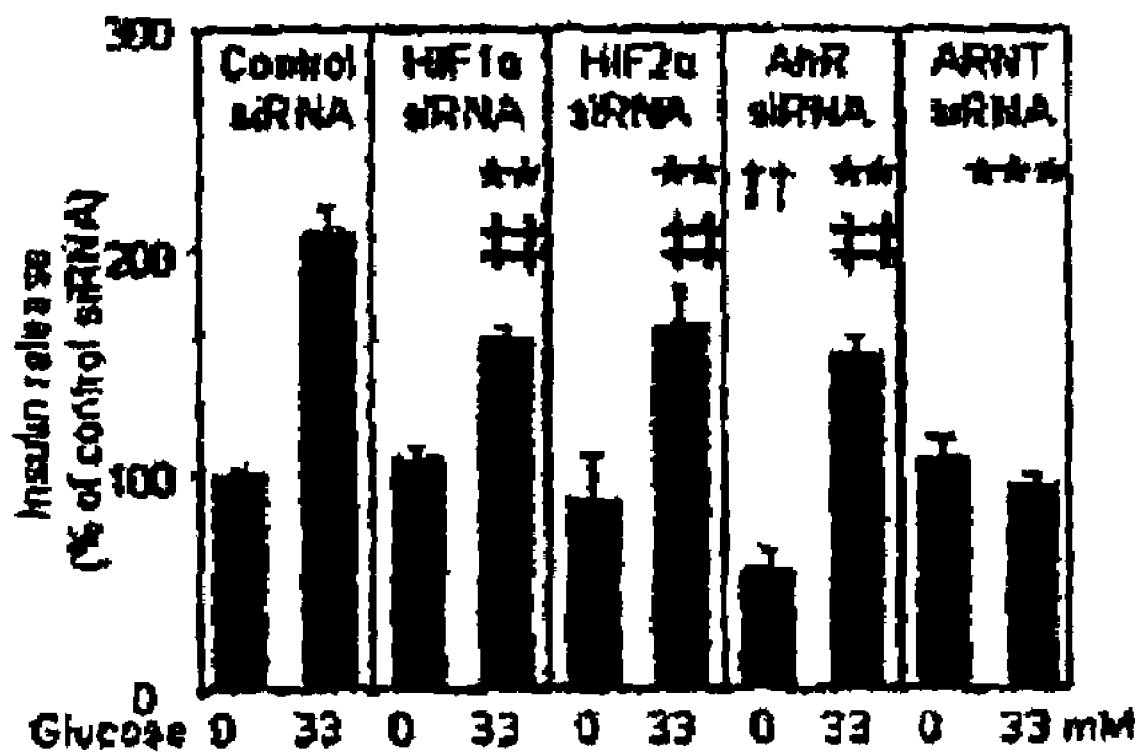
FIG. 5F is a panel of five bar graphs showing insulin release measured after RNAi treatment. AhR RNAi decreased basal insulin secretion, and RNAi directed against HIF1α, HIF2α and AhR all significantly decreased insulin release at 33 mM glucose, however, none of these were as effective as ARNT knockdown. $*=p<0.05$, $=p<0.01$ versus control, $*=p<0.001$, $††=p<0.01$ versus control at 0 mM glucose, $‡‡=p<0.01$ versus ARNT siRNA 30 mM glucose. Error bars are ±1 SEM.

Decreasing ARNT Expression with the Use of Small Interfering RNA (siRNA) In Vitro Results in an Impairment of Glucose-Stimulated Insulin Secretion In Min6 cells, HIF1α, HIF2α and AhR were clearly detectable at the mRNA level, and by Western blotting. To examine which of these ARNT partner(s) were important in the effect upon β-cell function, Min6 cells were treated with siRNAs directed against HIF1α, HIF2α, or AhR. Each of these was effective, achieving >65% decrease in expression (FIG. 5E). The effect of this reduction on glucose stimulated insulin release (GSIS) was then evaluated. At low glucose concentration, knockdown of the AhR led to a small, but significant decrease in insulin release, whereas knockdown of HIF1α and HIF2α were without effect (FIG. 5F). At 33 mM glucose, knockdown of HIF1α, HIF2α and AhR each independently produced 50%, 28% and 25% decreases, respectively, in insulin release. These decreases were accompanied by decreased expression of the MODY genes HNF1 and HNF4, and glucose metabolic genes, the same genes which showed decreased expression with decreased ARNT. None of HIF1α, HIF2α or AhR achieved the same magnitude of decrease seen with ARNT knockdown (which caused >80% decrease in GSIS), suggesting that the effect of decreased ARNT may result, at least in part, from loss of function of multiple of these bHLH-PAS heterodimers in β-cells.

Combining RNAi (HIF1α+HIF2α, HIF1α+AhR or HIF2α+AhR) produced a ≧80% decrease in GSIS. Taken together, these results suggest that HIF1α, HIF2α, and AhR proteins may each contribute in combination with ARNT to normal β-cell function and that alterations in this family of transcription factors may play a role in human type 2 diabetes.

Example 10

Modulators of ARNT

This example describes the evaluation of specific agents that modulate the expression of ARNT.

Figure 6A:
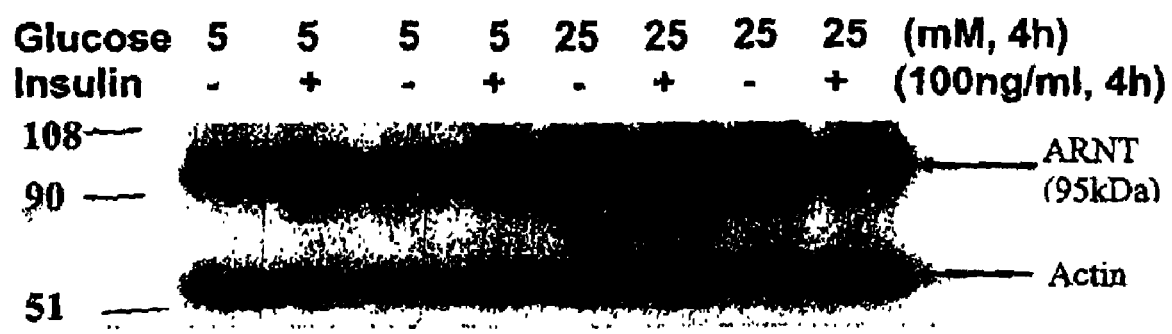
FIG. 6A is a Western immunoblot of an increase in ARNT expression, following treatment of Min6 cells with glucose and/or insulin.
Figure 6B:
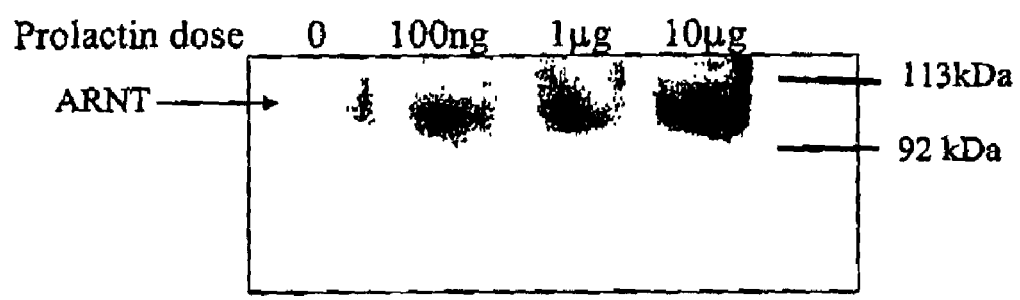
FIG. 6B is a Western immunoblot of an increase in ARNT expression, following treatment of Min6 cells with prolactin.

Min6 cells, a glucose responsive β-cell line, were treated with various agents to determine whether the agents can modulate ARNT expression. After treatment, cell lysates were analyzed by Western immunoblots. FIG. 6A shows that the addition of glucose (5 or 25 mM, 4 hours) and insulin (100 ng/ml, 4 hours) can increase ARNT expression. FIG. 6B shows that 4 hours of prolactin treatment (at 100 ng, 1 μg, or 10 μg) also stimulates ARNT expression.

These results show that it is possible to modulate ARNT expression, which would be beneficial in prevention or treatment of diabetes-related disorders.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a diabetes-related disorder selected from the group consisting of type I diabetes, type II diabetes, impaired glucose tolerance, insulin resistance, and beta cell dysfunction, the method comprising,
administering to the subject a therapeutically effective amount of a pharmaceutical composition comprising
an aryl hydrocarbon nuclear receptor translocator (ARNT) polypeptide comprising an amino acid sequence having at least 95% identity to SEQ ID NO:8, wherein the polypeptide binds the same DNA sequence that the full length protein binds to and can initiate transcription,
thereby treating the subject.

2. The method of claim 1, wherein the subject is human.

3. The method of claim 1, wherein the diabetes-related disorder is type I diabetes.

4. The method of claim 1, wherein the diabetes-related disorder is type II diabetes.

5. The method of claim 1, wherein the diabetes-related disorder is impaired glucose tolerance.

6. The method of claim 1, wherein the diabetes-related disorder is insulin resistance.

7. The method of claim 1, wherein the diabetes-related disorder is beta cell dysfunction.

8. A method of treating a subject having a diabetes-related disorder selected from the group consisting of type I diabetes, type II diabetes, impaired glucose tolerance, insulin resistance, and beta cell dysfunction, the method comprising, administering to the subject a therapeutically effective amount of a pharmaceutical composition comprising an active fragment of an ARNT polypeptide comprising SEQ ID NO:8, wherein the fragment binds the same DNA sequence that the full length protein bind to and can initiate transcription, thereby treating the subject.

9. The method of claim 8, wherein the active fragment comprises a basic DNA binding sequence, a PAS domain, and an HLH domain.

10. The method of claim 8, wherein the subject is human.

11. The method of claim 8, wherein the diabetes-related disorder is type I diabetes.

12. The method of claim 8, wherein the diabetes-related disorder is type II diabetes.

13. The method of claim 8, wherein the diabetes-related disorder is impaired glucose tolerance.

14. The method of claim 8, wherein the diabetes-related disorder is insulin resistance.

15. The method of claim 8, wherein the diabetes-related disorder is beta cell dysfunction.

* * * * *

UNITED STATES PATENT AND TRADEMARK OFFICE
CERTIFICATE OF CORRECTION

PATENT NO. : 7,700,555 B2  Page 1 of 1
APPLICATION NO. : 11/653594
DATED : April 20, 2010
INVENTOR(S) : Jenny Gunton It is certified that error appears in the above-identified patent and that said Letters Patent is hereby corrected as shown below:

On the Title Page, Column 1 ((30) Foreign Application Priority Data), Line 1, delete "Nov. 4, 2004" and insert -- Nov. 21, 2006 --

On the Title Page, Column 1 (Other Publications), Line 3, delete "www.nlm.nig.gov/" and insert -- www.nlm.nih.gov/ --

Signed and Sealed this

Third Day of August, 2010

David J. Kappos
*Director of the United States Patent and Trademark Office*